(12) United States Patent
Teramura

(10) Patent No.: US 10,362,928 B2
(45) Date of Patent: Jul. 30, 2019

(54) IMAGE PROCESSING APPARATUS AND IMAGE PROCESSING METHOD

(71) Applicant: FUJIFILM Corporation, Tokyo (JP)

(72) Inventor: Yuichi Teramura, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 47 days.

(21) Appl. No.: 15/794,189

(22) Filed: Oct. 26, 2017

(65) Prior Publication Data
US 2018/0042468 A1 Feb. 15, 2018

Related U.S. Application Data

(63) Continuation of application No. PCT/JP2016/062349, filed on Apr. 19, 2016.

(30) Foreign Application Priority Data

Apr. 30, 2015 (JP) .................................. 2015-093413

(51) Int. Cl.
*A61B 1/05* (2006.01)
*A61B 1/045* (2006.01)
(Continued)

(52) U.S. Cl.
CPC ............ *A61B 1/05* (2013.01); *A61B 1/00009* (2013.01); *A61B 1/045* (2013.01);
(Continued)

(58) Field of Classification Search
CPC ....... A61B 1/05; A61B 1/00009; A61B 1/045; G02B 23/2438; G02B 23/2476;
(Continued)

(56) References Cited

U.S. PATENT DOCUMENTS

2011/0077462 A1  3/2011  Saitou et al.
2011/0157424 A1  6/2011  Makino et al.
(Continued)

FOREIGN PATENT DOCUMENTS

CN  101175435 A  5/2008
CN  103037751 A  4/2013
(Continued)

OTHER PUBLICATIONS

International Search Report of PCT/JP2016/062349 dated Jul. 26, 2016 [PCT/ISA/210].
(Continued)

*Primary Examiner* — Nguyen T Truong
(74) *Attorney, Agent, or Firm* — Sughrue Mion, PLLC

(57) ABSTRACT

There is provided an image processing apparatus, method, and program for an endoscope image having a high degree of freedom of color assignment according to the shape feature of a structure. A structure region image is generated by extracting one or more structure regions from an image signal obtained by imaging an observation target in the living body. A shape feature amount of the structure region is calculated based on the structure region image, and a color corresponding to the feature amount is assigned to the structure region. A reduced original image is generated by performing processing for reducing at least one of the color or the contrast on an original image in which the observation target is drawn in color. A composite image is generated by superimposing the reduced original image and the structure region image subjected to the color assignment.

11 Claims, 20 Drawing Sheets

(51) Int. Cl.
| | |
|---|---|
| G02B 23/24 | (2006.01) |
| G06K 9/34 | (2006.01) |
| G06K 9/40 | (2006.01) |
| G06K 9/46 | (2006.01) |
| G06T 11/00 | (2006.01) |
| H04N 5/225 | (2006.01) |
| H04N 5/232 | (2006.01) |
| H04N 5/235 | (2006.01) |
| H04N 5/272 | (2006.01) |
| H04N 9/04 | (2006.01) |
| A61B 1/00 | (2006.01) |
| G06T 7/00 | (2017.01) |
| A61B 1/04 | (2006.01) |
| G02B 23/26 | (2006.01) |
| G06K 9/20 | (2006.01) |
| A61B 1/06 | (2006.01) |

(52) U.S. Cl.
CPC ..... *G02B 23/2438* (2013.01); *G02B 23/2476* (2013.01); *G02B 23/2484* (2013.01); *G06K 9/34* (2013.01); *G06K 9/40* (2013.01); *G06K 9/46* (2013.01); *G06T 7/0012* (2013.01); *G06T 11/001* (2013.01); *H04N 5/2256* (2013.01); *H04N 5/2354* (2013.01); *H04N 5/23229* (2013.01); *H04N 5/23245* (2013.01); *H04N 5/23293* (2013.01); *H04N 5/272* (2013.01); *H04N 9/045* (2013.01); *A61B 1/00188* (2013.01); *A61B 1/041* (2013.01); *A61B 1/043* (2013.01); *A61B 1/063* (2013.01); *A61B 1/0638* (2013.01); *A61B 1/0669* (2013.01); *A61B 1/0684* (2013.01); *G02B 23/2461* (2013.01); *G02B 23/26* (2013.01); *G06K 9/2027* (2013.01); *G06K 2209/051* (2013.01); *G06T 2207/10024* (2013.01); *G06T 2207/10068* (2013.01); *G06T 2207/30028* (2013.01); *G06T 2207/30096* (2013.01); *G06T 2207/30101* (2013.01)

(58) Field of Classification Search
CPC ........ G02B 23/2484; G06K 9/34; G06K 9/40; G06K 9/46; G06T 7/0012; G06T 11/001; H04N 5/2256; H04N 5/23229; H04N 5/23245; H04N 5/23293; H04N 5/2354
USPC .......................................................... 348/65
See application file for complete search history.

(56) References Cited

U.S. PATENT DOCUMENTS

| | | |
|---|---|---|
| 2012/0002879 A1 | 1/2012 | Kanda et al. |
| 2012/0307028 A1 | 12/2012 | Kanamori |
| 2013/0208958 A1 | 8/2013 | Tomoto |

FOREIGN PATENT DOCUMENTS

| | | |
|---|---|---|
| JP | 2011-218135 A | 11/2011 |
| JP | 2011-250925 A | 12/2011 |
| JP | 2012-011137 A | 1/2012 |
| JP | 5326064 B2 | 10/2013 |
| JP | 2014-124333 A | 7/2014 |

OTHER PUBLICATIONS

International Preliminary Report on Patentability of PCT/JP2016/062349 dated May 8, 2017 [PCT/IPEA/409].
Written Opinion of PCT/JP2016/062349 dated Jul. 26, 2016 [PCT/ISA/237].
Communication dated Mar. 28, 2019, from the China National Intellectual Property Administration in counterpart Application No. 201680024706.9.

IMAGE PROCESSING APPARATUS AND IMAGE PROCESSING METHOD

CROSS-REFERENCE TO RELATED APPLICATIONS

This application is a Continuation of PCT International Application No. PCT/JP2016/062349 filed on Apr. 19, 2016, which claims priority under 35 U.S.C § 119(a) to Japanese Patent Application No. 2015-093413 filed on Apr. 30, 2015. The above application is hereby expressly incorporated by reference, in its entirety, into the present application.

BACKGROUND OF THE INVENTION

1. Field of the Invention

The present invention relates to an image processing apparatus and an image processing method for processing an image signal obtained by an endoscope system.

2. Description of the Related Art

In the medical field, examination or diagnosis using an endoscope system for imaging an observation target in a living body has been widely performed. In order to assist the diagnosis based on an endoscope image captured by the endoscope system, a special light observation technique of acquiring a special light image, in which blood vessels are emphasized, by imaging the observation target with narrow-band special light having a narrow wavelength band or an image processing technique of generating an observation image, in which structures such as blood vessels of the observation target are emphasized, by performing image processing on a normal image captured with white light has also been developed (JP5326064B: corresponding to US 2013208958A1).

The image processing apparatus disclosed in JP5326064B extracts a plurality of structure regions, from which structures such as blood vessels are drawn, in a normal image obtained by imaging the mucosal surface, classifies the plurality of extracted structure regions into basic patterns, such as lines or circles, and generates a pseudo-color image in which different colors are assigned to the respective classified basic patterns. By assigning different colors to the respective basic patterns, it is possible to visually grasp how the basic patterns are distributed (paragraph 0028).

Since the shape features of structures, such as blood vessels in the mucosa, are important factors in the case of making a diagnosis, a technique for facilitating the grasping of the shape features of such structures is very useful.

However, since the normal image captured with white light is a color image (also referred to as a full color image) showing natural colors, there are restrictions on colors that can be used in the method of generating a pseudo-color image by assigning colors to the color image. For this reason, there is a problem that the number of assignable colors is small and accordingly the degree of freedom of color assignment is low.

The mucosa of the digestive tract has a plurality of structures, such as blood vessels or gland ducts. In addition, even if only the gland duct structure (referred to as a pit pattern or the like) of the large intestine is considered, the gland duct structures show different shape features depending on the condition of the tumor. Therefore, classification into a plurality of types is possible. Such shape features may be difficult to recognize in a normal image captured with white light. Therefore, it is preferable to assign different colors according to the shape features so that the features can be visually distinguished. Since the number of colors to be assigned is insufficient in a case where the degree of freedom of color assignment is low, effective color-coding cannot be performed.

SUMMARY OF THE INVENTION

It is an object of the present invention to provide an image processing apparatus and an image processing method for an endoscope image having a high degree of freedom of color assignment according to the shape feature of a structure.

An image processing apparatus of the present invention comprises an image signal acquisition unit, an original image generation unit, a reduced original image generation unit, a structure region image generation unit, a feature amount calculation unit, a color assignment unit, and an image combining unit. The image signal acquisition unit acquires an image signal obtained by imaging an observation target in a living body. The original image generation unit generates an original image in which the observation target is drawn in color based on the image signal. The reduced original image generation unit generates a reduced original image by performing processing for reducing at least one of a color or a contrast on the original image. The structure region image generation unit generates a structure region image in which one or more structure regions are extracted from the acquired image signal. The feature amount calculation unit calculates a shape feature amount of the structure region based on the structure region image. The color assignment unit assigns a color corresponding to the feature amount to the structure region. The image combining unit generates a composite image by superimposing the reduced original image and the structure region image subjected to the color assignment.

It is preferable that the color assignment unit changes a color assigned to the structure region stepwise or continuously according to the feature amount.

It is preferable that the structure region image generation unit generates a first structure region image showing a first structure region and a second structure region image showing a second structure region.

It is preferable that the color assignment unit assigns different colors to the first structure region image and the second structure region image.

It is preferable that the image combining unit generates, as the composite image, a first composite image obtained by combining the first structure region image and the reduced original image and a second composite image obtained by combining the second structure region image and the reduced original image.

It is preferable that the image combining unit generates, as the composite image, a third composite image obtained by combining three images of the first structure region image, the second structure region image, and the reduced original image.

It is preferable that the image combining unit uses the reduced original image common to the first composite image and the second composite image.

It is preferable that the reduced original image generation unit generates a first reduced original image and a second reduced original image and that the image combining unit uses the first reduced original image for the first composite image and uses the second reduced original image for the second composite image.

It is preferable that the color assignment unit makes a plurality of items of the feature amount correspond to any one of three axes on a three-dimensional color space and determines a position on the color space according to a specific value of each item of the feature amount to determine a color.

It is preferable that the color assignment unit performs gamma conversion in a case of determining a position on the color space according to the feature amount.

It is preferable to comprise a display control unit that performs control to display the composite image on a display screen.

It is preferable that, on the display screen, the original image and the composite image can be displayed in parallel or selectively.

It is preferable that the display control unit can output the display screen to a multi-monitor.

An image processing method of the present invention comprises an image signal acquisition step, a structure region image generation step, a feature amount calculation step, a color assignment step, and an image combining step. In the image signal acquisition step, an image signal obtained by imaging an observation target in a living body is acquired. In the structure region image generation step, a structure region image in which one or more structure regions are extracted from the acquired image signal is generated. In the feature amount calculation step, a shape feature amount of the structure region is calculated based on the structure region image. In the color assignment step, a color corresponding to the feature amount is assigned to the structure region. In the image combining step, a composite image is generated by superimposing a reduced original image, which is obtained by performing processing for reducing at least one of a color or a contrast on an original image in which the observation target is drawn in color based on the image signal, and the structure region image subjected to the color assignment.

According to the present invention, it is possible to provide an image processing apparatus and an image processing method for an endoscope image having a high degree of freedom of color assignment according to the shape feature of a structure.

DESCRIPTION OF THE PREFERRED EMBODIMENTS

First Embodiment

Figure 1:
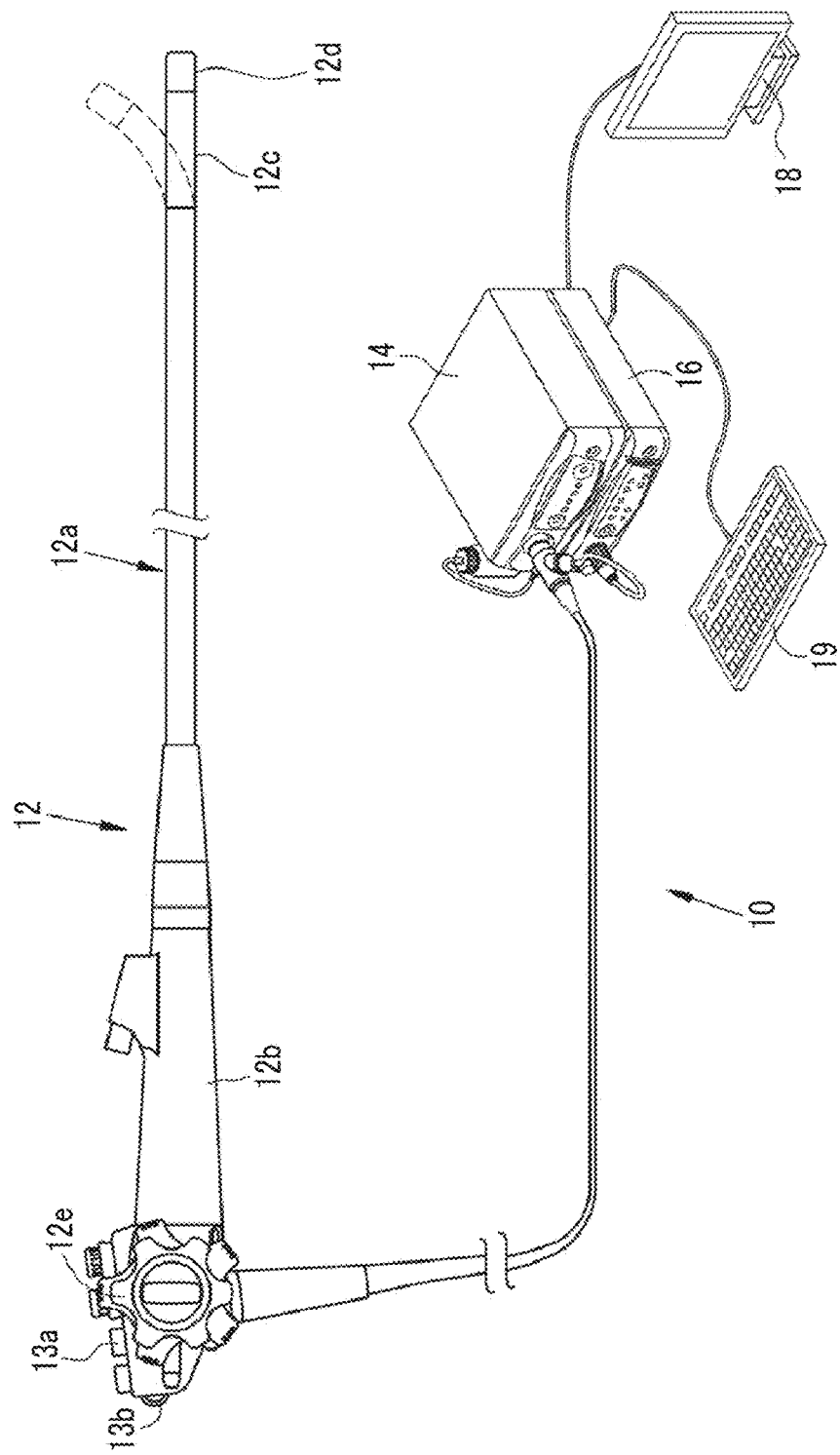
FIG. 1 is an external view of an endoscope system.

As shown in FIG. 1, an endoscope system 10 includes an endoscope 12, a light source device 14, a processor device 16, a monitor 18, and a console 19. The endoscope 12 is optically connected to the light source device 14, and is electrically connected to the processor device 16. The endoscope 12 includes an insertion unit 12a that is inserted into a living body, an operation unit 12b provided in a proximal end portion of the insertion unit 12a, and a bending portion 12c and a distal end portion 12d that are provided on the distal end side of the insertion unit 12a. By operating an angle knob 12e of the operation unit 12b, the bending portion 12c is bent. Through the bending operation, the distal end portion 12d is directed in a desired direction.

In addition to the angle knob 12e, a mode selector switch (SW) 13a and a zoom operation unit 13b are provided in the operation unit 12b. The mode selector SW 13a is used for a switching operation between two modes of a normal observation mode and a special observation mode. The normal observation mode is a mode in which a normal image is displayed on the monitor 18. The special observation mode is a mode in which a special image is displayed on the monitor 18 in addition to the normal image. Two or more modes may be prepared as observation modes. In the special observation mode, only the special image may be displayed without displaying the normal image.

The normal image is a color image captured by using white light as illumination light. The color image captured with white light is also generally referred to as a full color image since the subject is drawn in natural color and. Here, being captured with white light includes a case of being captured with illumination light corresponding to white light by combining light beams having wavelength bands of at least three colors of a blue component, a green component, and a red component, which form the white light, using a plurality of light sources that emit the light beams having the wavelength bands of at least three colors of the blue component, the green component, and the red component, respectively, as will be described later. Needless to say, being captured with white light includes a case of being captured with broadband light including all the wavelength bands of the blue component, the green component, and the red component forming the white light.

As will be described later, the special image is an image in which a structure region, which is a region where blood vessels in a mucosa, gland ducts of the mucosal surface, and the like are drawn, is emphasized. The zoom operation unit 13b enlarges or reduces the observation target being displayed on the monitor 18 by moving a zoom lens 47 (refer to FIG. 2) between the telephoto position and the wide position.

The processor device 16 is electrically connected to the monitor 18 and the console 19. The monitor 18 outputs and displays image information or the like. The console 19 functions as a user interface (UI) for receiving an input operation, such as a function setting. An external recording unit (not shown) in which image information and the like are recorded may be connected to the processor device 16.

Figure 2:
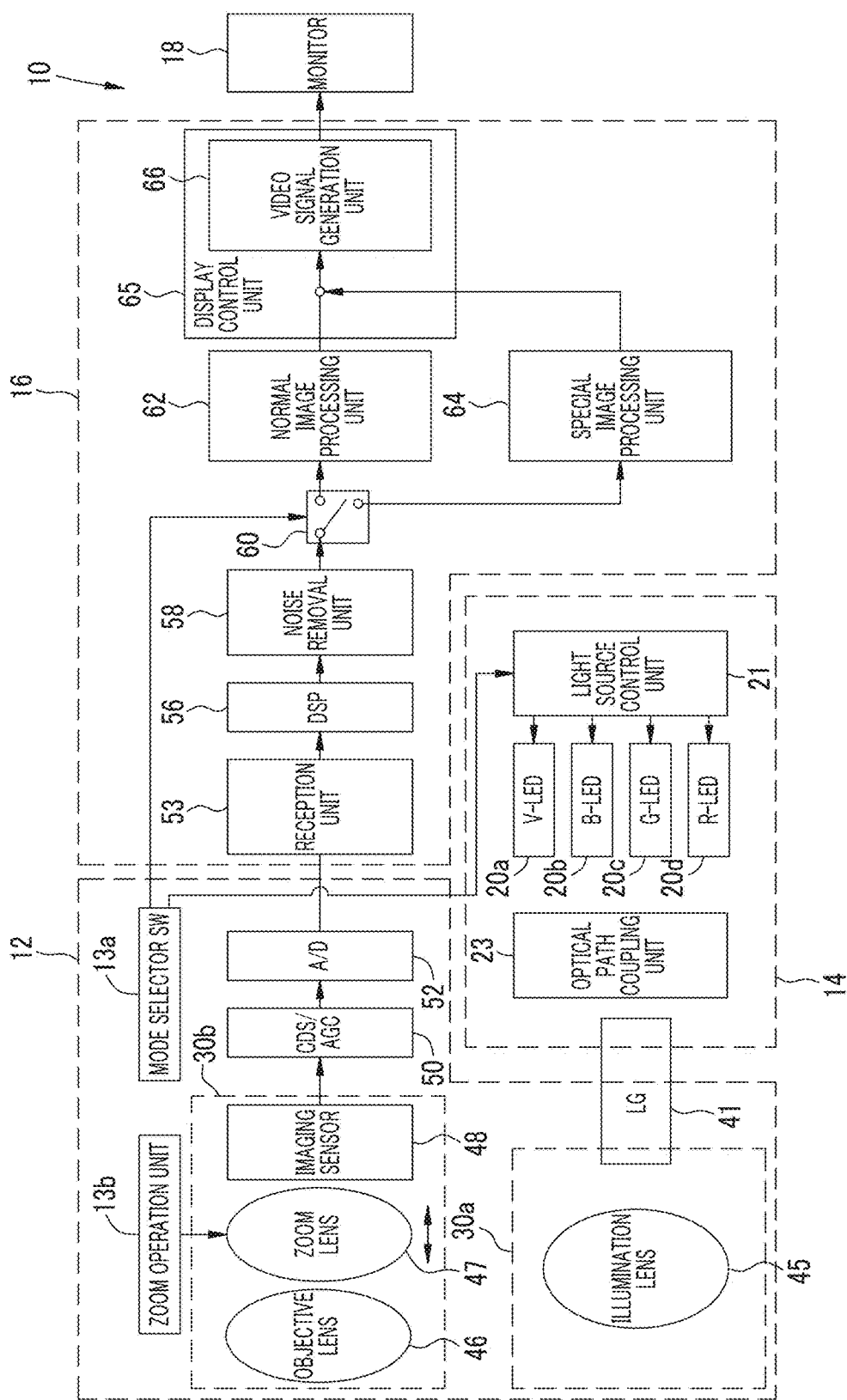
FIG. 2 is a block diagram showing a function of the endoscope system.

As shown in FIG. 2, the light source device 14 includes a violet light emitting diode (V-LED) 20a, a blue light emitting diode (B-LED) 20b, a green light emitting diode (G-LED) 20c, a red light emitting diode (R-LED) 20d, a light source control unit 21 that controls the driving of the LEDs 20a to 20d of four colors, and an optical path coupling unit 23 for coupling the optical paths of light beams of four colors emitted from the LEDs 20a to 20d of four colors. The light beams coupled by the optical path coupling unit 23 are emitted into the living body through a light guide (LG) 41 inserted in the insertion unit 12a and an illumination lens 45. Instead of the LED, a laser diode (LD) may be used.

Figure 3:
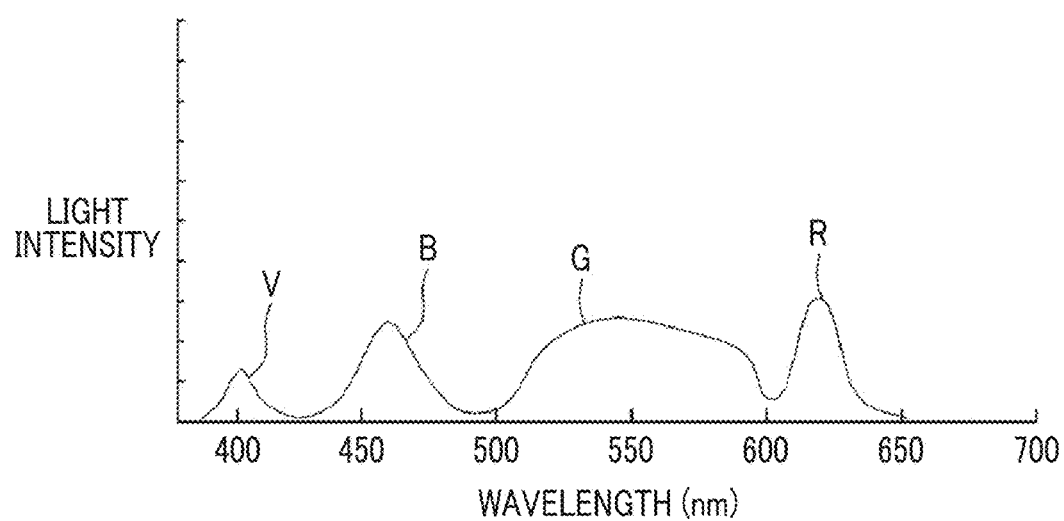
FIG. 3 is a graph showing the emission spectrum of violet light V, blue light B, green light G, and red light R.

As shown in FIG. 3, the V-LED 20a generates violet light V having a center wavelength of 405±10 nm and a wavelength range of 380 to 420 nm. The B-LED 20b generates blue light B having a center wavelength of 460±10 nm and a wavelength range of 420 to 500 nm. The G-LED 20c generates green light G having a wavelength range of 480 to 600 nm. The R-LED 20d generates red light R having a center wavelength of 620 to 630 nm and a wavelength range of 600 to 650 nm.

The light source control unit 21 turns on the V-LED 20a, the B-LED 20b, the G-LED 20c, and the R-LED 20d in both the normal observation mode and the special observation mode. Accordingly, light in which light beams of four colors of the violet light V, the blue light B, the green light G, and the red light R are mixed is emitted to the observation target. The light source control unit 21 controls the LEDs 20a to 20d so that the light amount ratio among the violet light V, the blue light B, the green light G, and the red light R becomes Vc:Bc:Gc:Rc.

As shown in FIG. 2, the light guide (LG) 41 is built into the endoscope 12 and a universal cord (cord for connecting the endoscope 12 to the light source device 14 and the processor device 16), and makes the light coupled by the optical path coupling unit 23 propagate to the distal end portion 12d of the endo scope 12.

An illumination optical system 30a and an imaging optical system 30b are provided in the distal end portion 12d of the endoscope 12. The illumination optical system 30a has the illumination lens 45, and the light from the light guide 41 is emitted to the observation target through the illumination lens 45. The imaging optical system 30b includes an objective lens 46, a zoom lens 47, and an imaging sensor 48.

The imaging sensor 48 images the observation target, and outputs an image signal obtained by the imaging. Specifically, reflected light from the observation target is incident on the imaging sensor 48 through the objective lens 46 and the zoom lens 47. As a result, a reflected image of the observation target is formed on the imaging surface of the imaging sensor 48. The imaging sensor 48 outputs an image signal corresponding to the formed reflected image.

The imaging sensor 48 is, for example, a charge coupled device (CCD) imaging sensor or a complementary metal-oxide semiconductor (CMOS) imaging sensor. The imaging sensor 48 used in the present invention is a color imaging sensor for obtaining RGB image signals of three colors of red (R), green (G), and blue (B), that is, a so-called RGB imaging sensor having an R pixel in which an R filter is provided, a G pixel in which a G filter is provided, and a B pixel in which a B filter is provided as a plurality of pixels forming an imaging surface.

As the imaging sensor 48, a so-called complementary color imaging sensor including complementary color filters of cyan (C), magenta (M), yellow (Y), and green (G) may be used instead of the RGB color imaging sensors. In the case of using the complementary color imaging sensor, image signals of four colors of CMYG are output. Therefore, it is necessary to convert the image signals of four colors of CMYG into image signals of three colors of RGB by complementary color-primary color conversion. The imaging sensor 48 may also be a monochrome imaging sensor in which no color filter is provided. In this case, the light source control unit 21 needs to turn on the blue light B, the green light G, and the red light R in a time-division manner and apply synchronization processing in processing on the imaging signal.

The image signal output from the imaging sensor 48 is transmitted to a CDS/AGC circuit 50. The CDS/AGC circuit 50 performs correlated double sampling (CDS) or auto gain control (AGC) for the image signal that is an analog signal. The image signal having passed through the CDS/AGC circuit 50 is converted into a digital image signal by an analog/digital converter (A/D converter) 52. The digital image signal after A/D conversion is input to the processor device 16.

The processor device 16 includes a reception unit 53, a digital signal processor (DSP) 56, a noise removal unit 58, an image processing switching unit 60, a normal image processing unit 62, a special image processing unit 64, a display control unit 65, and a video signal generation unit 66. The reception unit 53 receives digital RGB image signals from the endoscope 12. The R image signal corresponds to a signal output from the R pixel of the imaging sensor 48, the G image signal corresponds to a signal output from the G pixel of the imaging sensor 48, and the B image signal corresponds to a signal output from the B pixel of the imaging sensor 48.

The DSP 56 performs various kinds of signal processing, such as defect correction processing, offset processing, gain correction processing, linear matrix processing, gamma conversion processing, and demosaic processing, on the received image signals. By the defect correction processing, the signal of the defective pixel of the imaging sensor 48 is corrected. In the offset processing, a dark current component is removed from the RGB image signals subjected to the defect correction processing, and the exact zero level is set.

In the gain correction processing, the signal level is adjusted by multiplying each of the RGB image signals after the offset processing by a specific gain. Linear matrix processing for increasing color reproducibility is performed on the RGB image signals after the gain correction processing. Then, the brightness or saturation is adjusted by gamma conversion processing. Demosaic processing (also referred to as isotropic processing or pixel interpolation processing) is performed on the RGB image signals after the linear matrix processing, and the signal of missing color in each pixel is generated by interpolation. Through the demosaic processing, all pixels have signals of RGB colors.

The noise removal unit 58 removes noise from the RGB image signals by performing noise removal processing (for example, a moving average method or a median filter method) on the RGB image signals subjected to the gamma correction or the like by the DSP 56. The RGB image signals after removing noise is transmitted to the image processing switching unit 60. Here, the "image signal acquisition unit" of the present invention corresponds to a configuration including the reception unit 53, the DSP 56, and the noise removal unit 58.

The image processing switching unit 60 transmits the RGB image signals to the normal image processing unit 62 in a case where the normal observation mode is set by the mode selector SW 13a, and transmits the RGB image signals to the special image processing unit 64 in a case where the special observation mode is set.

The normal image processing unit 62 performs color conversion processing, color enhancement processing, and structure enhancement processing on the RGB image signals. In the color conversion processing, 3×3 matrix processing, gradation conversion processing, three-dimensional LUT processing, and the like are performed on the digital RGB image signals, so that the digital RGB image signals are converted into RGB image signals subjected to color conversion processing. Then, various kinds of color enhancement processing are performed on the RGB image signals after the color conversion processing. Structure enhancement processing, such as spatial frequency enhancement, is performed on the RGB image signals after the color enhancement processing. The RGB image signals subjected to the structure enhancement processing are input, as RGB image signals of a normal image for display, from the normal image processing unit 62 to the video signal generation unit 66.

The special image processing unit 64 generates a special image for display based on the RGB image signals. Details of the special image processing unit 64 will be described later. RGB image signals of the special image for display generated by the special image processing unit 64 are input to the video signal generation unit 66. Similarly to the normal image processing unit 62, the special image processing unit 64 may perform color conversion processing, color enhancement processing, and structure enhancement processing.

The display control unit 65 controls the display of the monitor 18. A display screen for displaying a normal image and a special image is displayed on the monitor 18. The display control unit 65 generates a display screen to be displayed on the monitor 18 by inserting a normal image or a special image into template data of the display screen. The display control unit 65 has the video signal generation unit 66. The video signal generation unit 66 converts the generated display screen into a video signal to be displayed on the monitor 18. Based on the video signal, the monitor 18 displays a display screen of a normal image and a special image.

Figure 4:
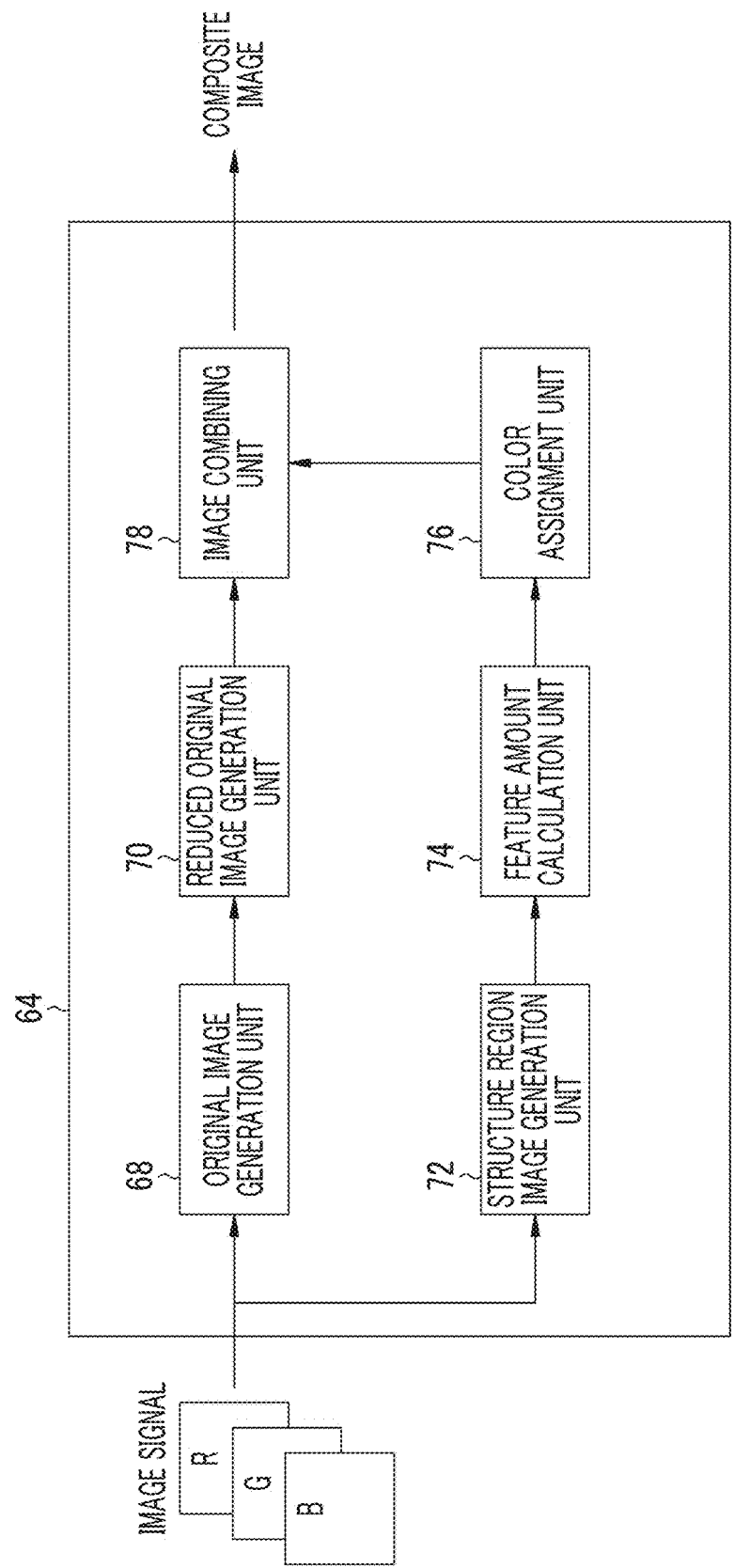
FIG. 4 is a block diagram showing a function of a special image processing unit.
Figure 5:
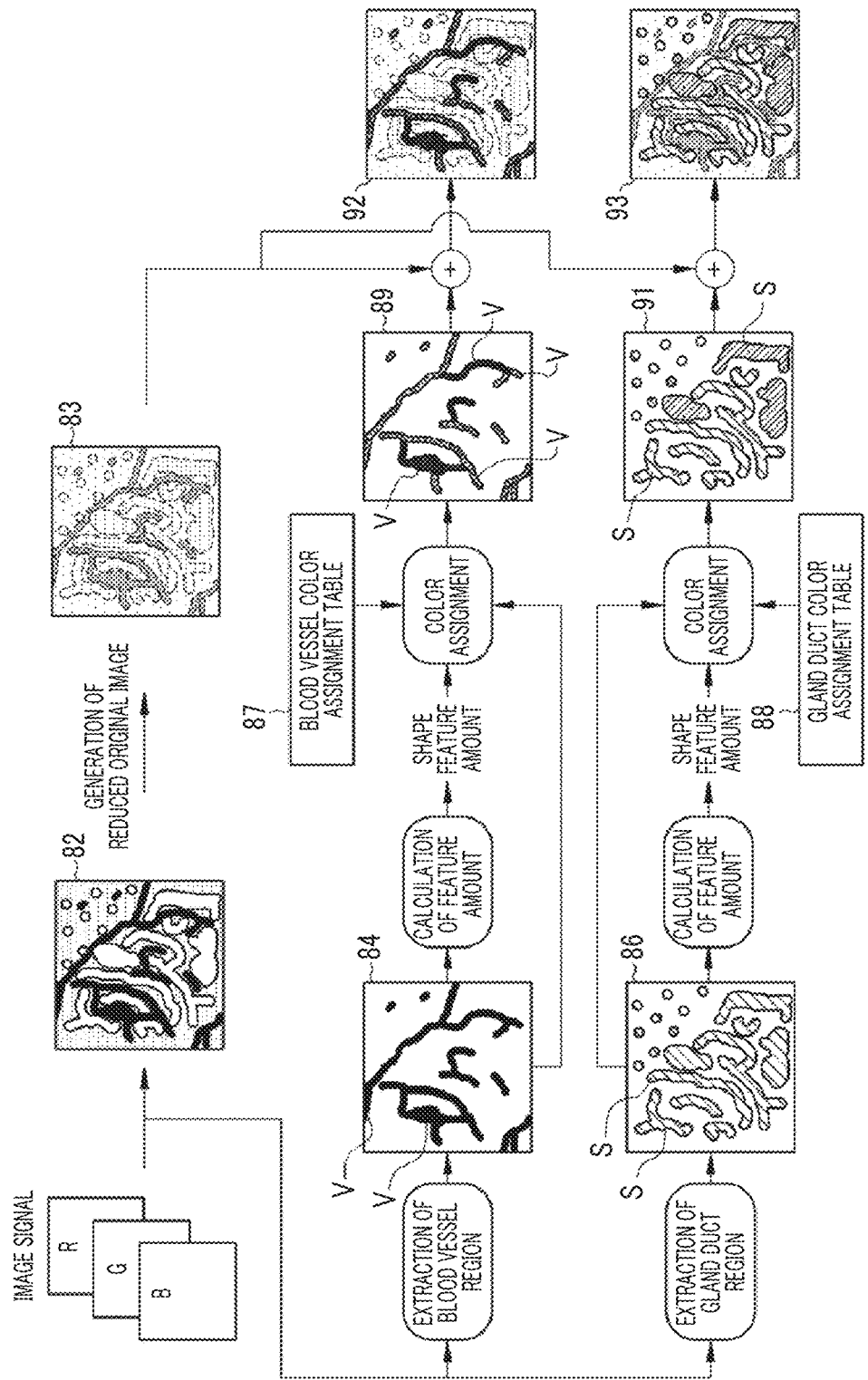
FIG. 5 is an explanatory diagram of special image processing.

As shown in FIG. 4, the special image processing unit 64 includes an original image generation unit 68, a reduced original image generation unit 70, a structure region image generation unit 72, a feature amount calculation unit 74, a color assignment unit 76, and an image combining unit 78. The special image processing unit 64 performs special image processing based on the RGB image signals, and outputs a composite image that is a special image. As shown in FIG. 5, the original image generation unit 68 generates a color original image based on the RGB image signals. An original image 82 is the same color image as the normal image, and is generated by the special image processing unit 64 in the same processing procedure as that of the normal image processing unit 62.

The reduced original image generation unit 70 generates a reduced original image 83 having reduced color and contrast as compared with the original image 82 by performing processing for reducing at least one of color or contrast on the original image 82. In this example, the reduced original image 83 is a monochrome image obtained by monochromatizing the color original image 82, and the color is reduced as compared with the original image 82 by monochromatization.

The reduced original image 83 is not a binary image but a gray scale image obtained by gray scale reduction. The number of gradations of each pixel of the original image 82 is, for example, 256 gradations. At the time of gray scale reduction, the reduced original image 83 is converted from 256 gradations of the original image 82 to 64 gradations to 192 gradations, so that the contrast is reduced. Thus, the reduced original image 83 in this example has reduced color and contrast as compared with the original image 82. The reduced original image 83 is used as a base image in the case of performing image combination to be described later.

The structure region image generation unit 72 generates a structure region image by extracting one or more structure regions from the image signal. The structure region is a region where structures such as blood vessels in a mucosa or gland ducts of the mucosal surface are drawn. The structure region is a blood vessel region (corresponding to a first structure region) in a case where the structure is a blood vessel, and the structure region is a gland duct region (corresponding to a second structure region) in a case where the structure is a gland duct. Specifically, as shown in FIG. 5, the structure region image generation unit 72 generates a blood vessel region image (corresponding to the first structure region image) 84 by performing blood vessel region extraction processing for extracting a blood vessel region, and generates a gland duct region image (corresponding to the second structure region image) 86 by extracting a gland duct region.

As an image signal for generating the blood vessel region image 84, for example, a B image signal is used. As is well known, hemoglobin in blood has a larger absorption rate for blue light than for red light or green light. By using a B image signal having a high contrast in a blood vessel region, it is easy to extract a blood vessel region. The blood vessel region appears as a region having a low brightness (high density) in the B image signal. The blood vessel region image 84 is a gray scale monochrome image generated by extracting a region having a low brightness (high density) from the B image signal.

As an image signal for generating the gland duct region image 86, for example, a G image signal having a large contrast in a gland duct region is used. Epithelial cells forming the mucosal surface have a three-dimensional structure with periodic folds. The gland duct region is a region having such a three-dimensional structure, and the surface structure is drawn by the difference in absorption and scattering of light between the surface and the recess of the fold. Compared with other color light components, green light is excellent in drawing of a three-dimensional effect. Therefore, a three-dimensional surface structure can be drawn with good contrast. In the G image signal, the surface of the fold in the gland duct region appears as a region having a high brightness (low density), and the recess of the fold appears as a region having a low brightness (high density). The gland duct region image 86 is a gray scale monochrome image generated by extracting a region having a high brightness (low density) from the G image signal.

Also in the gland duct region image 86, a blood vessel region is drawn even though the contrast is low. In the gland duct region image 86, the blood vessel region is noise. Therefore, in order to emphasize the gland duct region more, the blood vessel region may be removed from the gland duct region image 86. As a method of removal, for example, there is a method of removing a blood vessel region by specifying the position of the blood vessel region from the blood vessel region image 84 and interpolating the pixels of the blood vessel region specified in the gland duct region image 86 with surrounding pixels.

In the case of extracting a blood vessel region or a gland duct region, black hat filtering processing or top hat filtering processing may be used. The black hat filtering processing is processing for leaving only a region having a relatively low brightness (dark portion) by removing a region having a relatively high brightness (bright portion), and can be used in the case of extracting a blood vessel region. A gland duct region may be extracted by the top hat filtering processing for leaving only a region having a relatively high brightness (bright portion) by removing a region having a relatively low brightness (dark portion).

By such extraction processing, as shown in FIG. 5, the blood vessel region image 84 is a monochrome image in which only a blood vessel region V is drawn with high contrast, and the gland duct region image 86 is a monochrome image in which only a gland duct region S is drawn with high contrast.

The feature amount calculation unit 74 calculates the shape feature amount of a structure region based on the structure region image. In this example, the shape feature amount of each of the blood vessel region V and the gland duct region S is calculated based on the structure region image of each of the blood vessel region image 84 and the gland duct region image 86.

Figure 6:
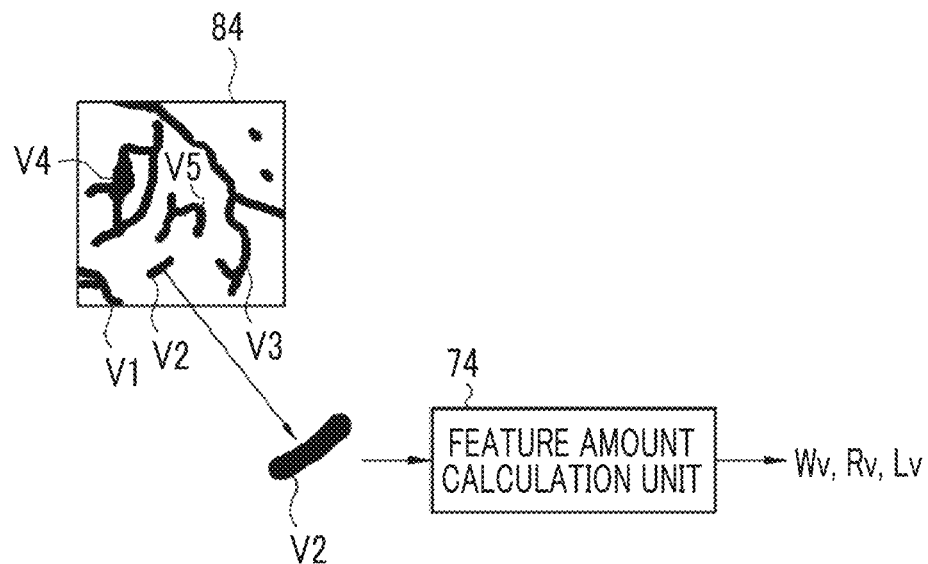
FIG. 6 is an explanatory diagram of processing for calculating the feature amount of a blood vessel region.
Figure 7:
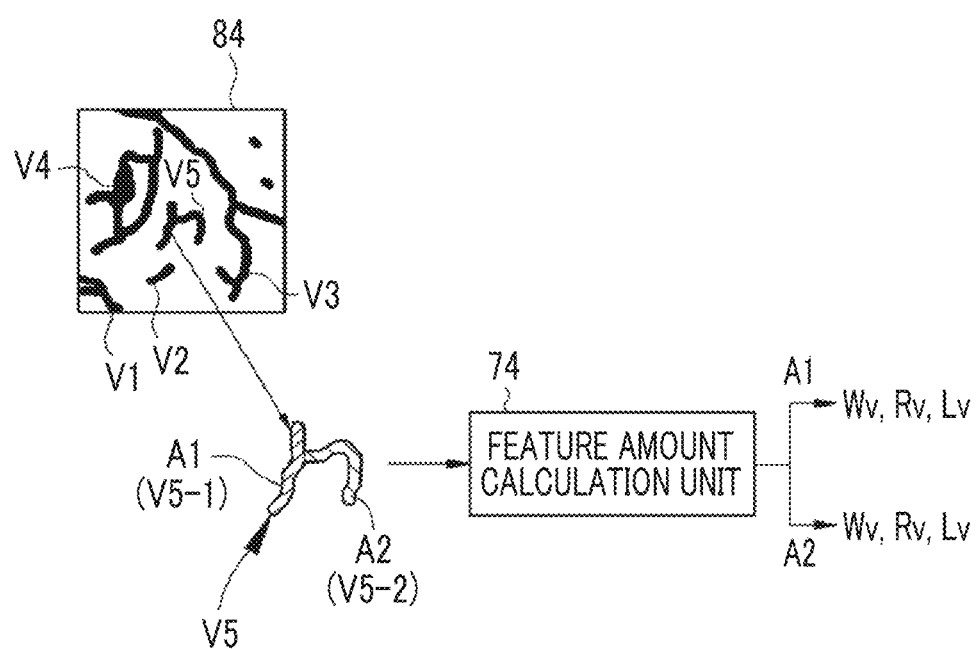
FIG. 7 is an explanatory diagram of processing for calculating the feature amount of a blood vessel region different from FIG. 6.

As shown in FIGS. 6 and 7, the feature amount calculation unit 74 extracts the blood vessel region V one by one from the blood vessel region image 84, and calculates a shape feature amount for each extracted blood vessel region V. Items of the shape feature amount of the blood vessel region V are, for example, a maximum width Wv, a minimum radius Rv, and a length Lv. The maximum width Wv is a width indicating the maximum value in the blood vessel region V for which calculation is to be performed. The minimum radius Rv is the radius of a bending place bent at the maximum curvature in a case where the blood vessel region V is bent. The length Lv is the length of the blood vessel region V in the longitudinal direction. In a case where the blood vessel region V is bent, the length Lv is, for example, the length of the center line in a case where the center line along the bending shape is assumed.

In addition to calculating the feature amount for each blood vessel region V1 formed by one closed region in the blood vessel region image 84 as shown in FIG. 6, the feature amount calculation unit 74 may divide one blood vessel region V5 formed by one closed region into a plurality of regions A1 and A2 and calculate a feature amount for each of the regions A1 and A2 as shown in FIG. 7. Whether to divide one blood vessel region V or not as described above is appropriately determined according to, for example, size or shape complexity. In this manner, for a plurality of structure regions in the structure region image, the feature amount calculation unit 74 calculates a feature amount for each structure region or for each of a plurality of regions obtained by dividing a structure region.

The feature amount calculation unit 74 calculates feature amounts for all the blood vessel regions V in the blood vessel region image 84. Then, the feature amount calculation unit 74 assigns one region number to one region for which the feature amount has been calculated. In the example shown in FIG. 6, one region number, for example, "V2", is assigned to one blood vessel region V2. In the example shown in FIG. 7, for example, region numbers with branch numbers, such as "V5-1" and "V5-2", are assigned to a plurality of regions A1 and A2 in one blood vessel region V5, respectively. The feature amount calculation unit 74 outputs a set of information in which a region number, coordinate information in the blood vessel region image 84, and the calculated feature amount are associated with each other for each region to which the region number is assigned.

Figure 8:
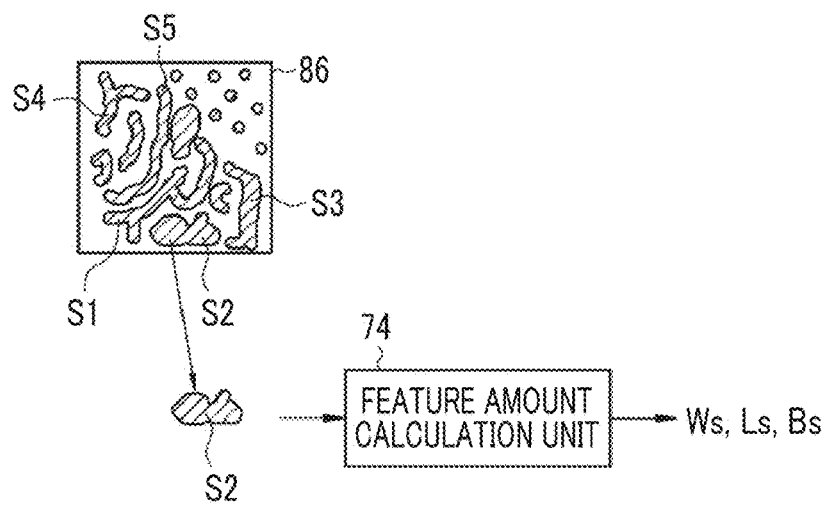
FIG. 8 is an explanatory diagram of processing for calculating the feature amount of a gland duct region.

As shown in FIG. 8, the feature amount calculation unit 74 extracts the gland duct region S one by one from the gland duct region image 86, and calculates a shape feature amount for each extracted gland duct region S, in the same manner as for the blood vessel region image 84. Items of the shape feature amount of the gland duct region S are, for example, a maximum width Ws, a long diameter Ls, and the number of branches Bs. The maximum width Ws is a width indicating the maximum value in the gland duct region S for which calculation is to be performed. The long diameter Ls is a maximum value of the length in a direction perpendicular to a short diameter assuming that the maximum width Ws is the short diameter. The number of branches Bs is the number of branches in a case where there is a branching region, such as a gland duct region S1.

The feature amount calculation unit 74 calculates a shape feature amount for one gland duct region S2 formed by one closed region in the gland duct region image 86. Also for the gland duct region S2, as shown for the blood vessel region V in FIG. 7, there is a case where one gland duct region S2 is divided into a plurality of regions and the feature amount is calculated for each of the divided regions. Whether to divide one gland duct region S or not is appropriately determined according to, for example, size or shape complexity.

As in the case of the blood vessel region image 84, the feature amount calculation unit 74 calculates feature amounts for all the gland duct regions S in the gland duct region image 86. Then, the feature amount calculation unit 74 assigns one region number to one region for which the feature amount has been calculated. In the example shown in FIG. 8, one region number, for example, "S2", is assigned to one gland duct region S2. Although not shown, in the case of calculating the feature amount by dividing one gland duct region S into a plurality of regions, region numbers with branch numbers are assigned to respective regions. The feature amount calculation unit 74 outputs a set of information in which a region number, coordinate information in the gland duct region image 86, and the calculated feature amount are associated with each other for each region to which the region number is assigned.

The color assignment unit 76 assigns a color corresponding to the calculated feature amount to the structure region for which the feature amount has been calculated. A blood vessel color assignment table 87 and a gland duct color assignment table 88 are stored in a memory in the special image processing unit 64. The color assignment unit 76 assigns a color to the blood vessel region V in the blood vessel region image 84 with reference to the blood vessel color assignment table 87, and assigns a color to the gland duct region S in the gland duct region image 86 with reference to the gland duct color assignment table 88.

Figure 9:
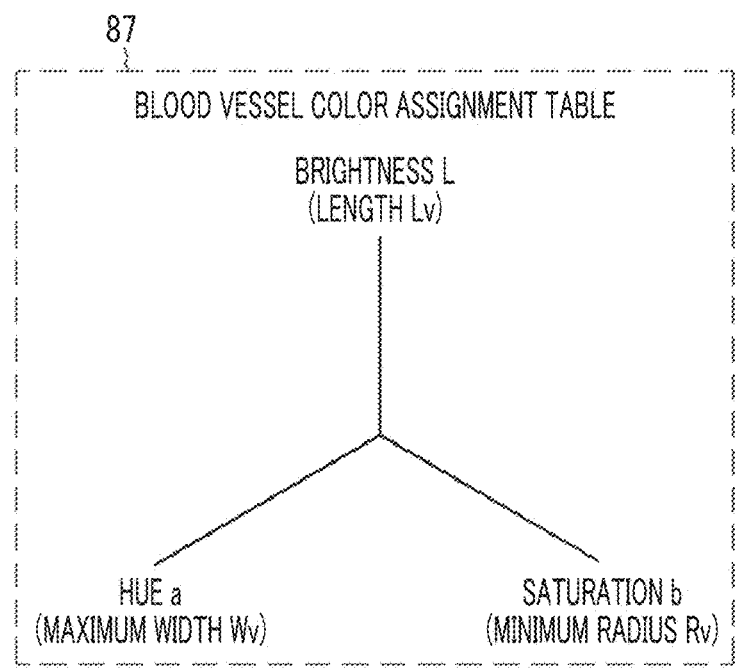
FIG. 9 is an explanatory diagram of a blood vessel color assignment table.

As shown in FIG. 9, the blood vessel color assignment table 87 is, for example, a three-dimensional look up table (LUT) generated based on the three-dimensional color space of the Lab color system. As is well known, the Lab color system is a color system in which brightness is shown by L and hue and chromaticity indicating saturation are shown by a and b. In the blood vessel color assignment table 87, three items of feature amounts, such as the maximum width Wv, the minimum radius Rv, and the length Lv of the blood vessel region V, correspond to the three axes of the Lab color system. Specifically, the maximum width Wv is assigned to the axis of the brightness L, the minimum radius Rv is assigned to the axis of the hue a, and the length Lv is assigned to the axis of the saturation b. In this example, the brightness L changes according to a change in the maximum width Wv, and the hue a and the saturation b change according to changes in the minimum radius Rv and the length Lv.

Figure 10:
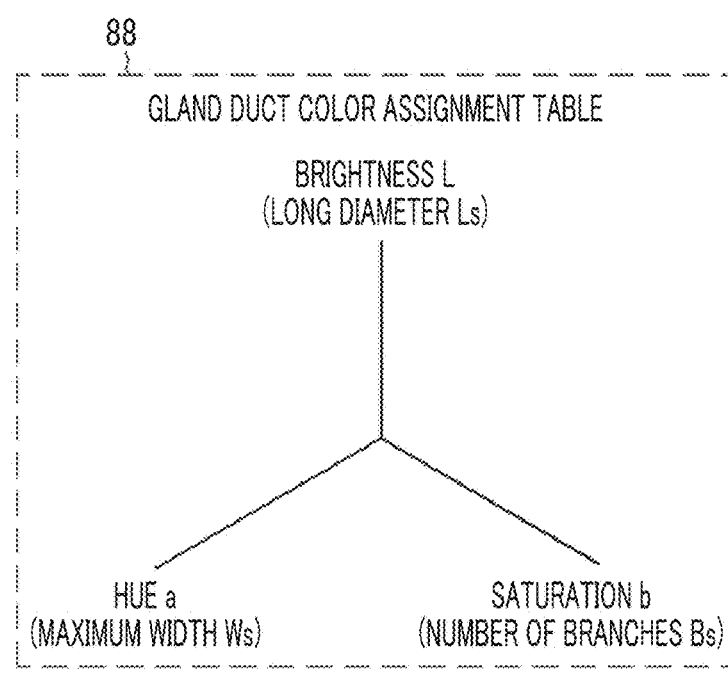
FIG. 10 is an explanatory diagram of a gland duct color assignment table.

As shown in FIG. 10, the gland duct color assignment table 88 is also a three-dimensional LUT generated based on the color space of the Lab color system. In the gland duct color assignment table 88, three feature amount items, such as the maximum width Ws, the long diameter Ls, and the number of branches Bs of the gland duct region S, correspond to the three axes of the Lab color system. Specifically, the maximum width Ws is assigned to the axis of the brightness L, the long diameter Ls is assigned to the axis of the hue a, and the number of branches Bs is assigned to the axis of the saturation b. In this example, the brightness L changes according to a change in the maximum width Ws, and the hue a and the saturation b change according to changes in the long diameter Ls and the number of branches Bs.

Figure 11:
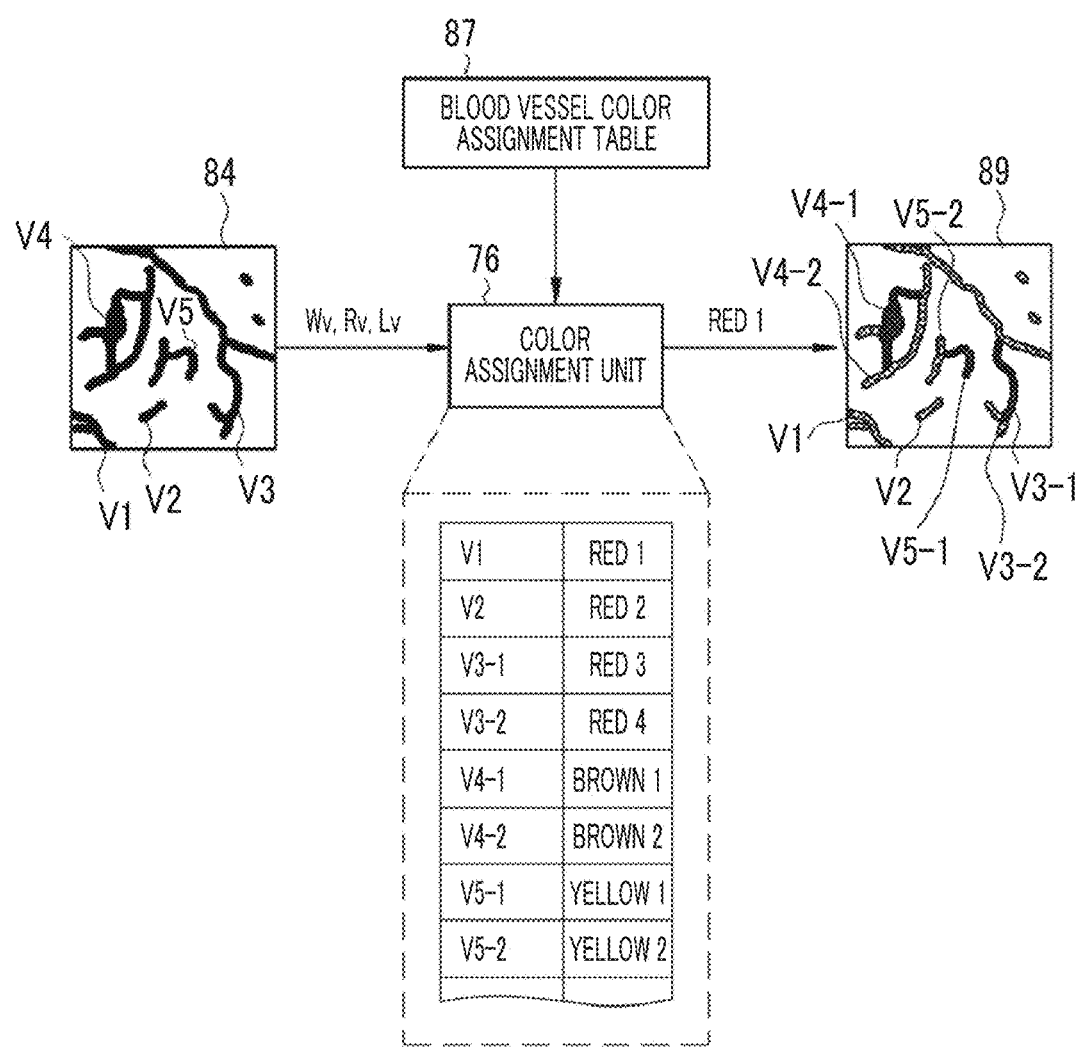
FIG. 11 is an explanatory diagram of color assignment processing on a blood vessel region.

As shown in FIG. 11, the color assignment unit 76 assigns a color to each blood vessel region V for which the feature amount has been calculated. In a case where the feature amount is calculated for each of a plurality of regions obtained by dividing one blood vessel region V5, such as the blood vessel regions V5-1 and V5-2, a color is assigned to each divided region. The color assignment unit 76 determines a position based on specific values of three items (Wv, Rv, Lv) of the feature amount on the color space of the blood vessel color assignment table 87, and determines the color of a region for which the feature amount has been calculated. By performing such processing for each blood vessel region V, a color is assigned to each of the blood vessel regions V1, V2, V3-1, V3-2, . . . .

In the example shown in FIG. 11, colors are assigned such that "red 1" is assigned to the blood vessel region V1, "red 2" is assigned to the blood vessel region V2, and "red 3" is assigned to the blood vessel region V3-1. Here, different numbers assigned to the colors, such as "red 1" and "red 2", indicate that the colors are based on the same color system but at least one of brightness, hue, or saturation is different.

The color assignment unit 76 specifies the position of each blood vessel region V in the blood vessel region image 84 based on the coordinate information acquired from the feature amount calculation unit 74, and colors each blood vessel region V with the assigned color. By performing such color assignment processing on all the blood vessel regions V for which the feature amount has been calculated, a pseudo-color blood vessel region image 89 in which the blood vessel region image 84 is pseudo-colored is generated. In the pseudo-color blood vessel region image 89, a plurality of blood vessel regions V are displayed in a color-coded manner according to the shape feature amount.

Figure 12:
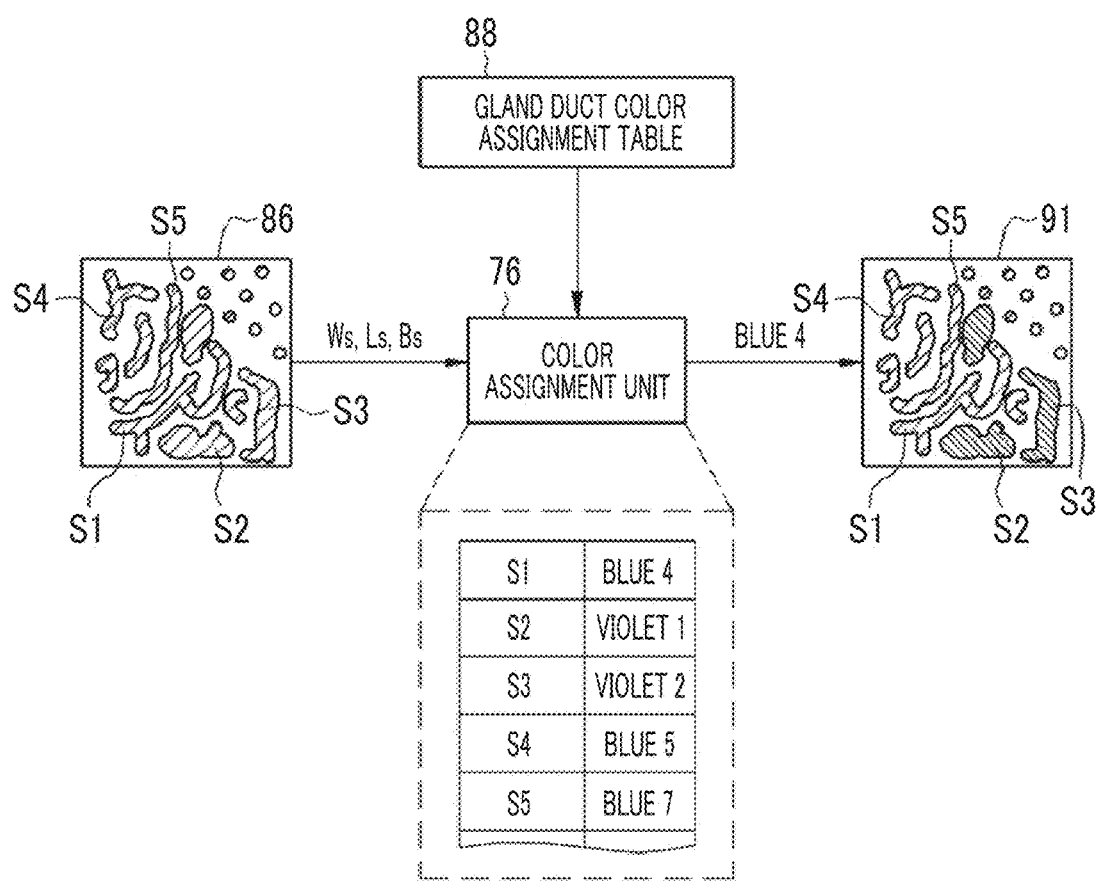
FIG. 12 is an explanatory diagram of color assignment processing on a gland duct region.

As shown in FIG. 12, the color assignment unit 76 assigns a color to each gland duct region S for which the feature amount has been calculated, in the same manner as for the blood vessel region V. The color assignment unit 76 determines a position based on the three feature amounts (Ws, Ls, Bs) on the color space of the gland duct color assignment table 88, and determines the color of a region for which the feature amount has been calculated. By performing such processing for each gland duct region S, a color is assigned to each of gland duct regions S1, S2, S3, S4, . . . .

In the example shown in FIG. 12, colors are assigned such that "blue 4" is assigned to the gland duct region S1, "violet 1" is assigned to the gland duct region S2, and "violet 2" is assigned to the gland duct region S3. Also in the example shown in FIG. 12, different numbers assigned to the colors, such as "violet 1" and "violet 2", indicate that the colors are based on the same color system but at least one of brightness, hue, or saturation is different.

The color assignment unit 76 specifies the position of each gland duct region S in the gland duct region image 86 based on the coordinate information acquired from the feature amount calculation unit 74, and colors each gland duct region S with the assigned color. By performing such color assignment processing on all the gland duct regions S for which the feature amount has been calculated, a pseudo-color gland duct region image 91 in which the gland duct region image 86 is pseudo-colored is generated. In the pseudo-color gland duct region image 91, a plurality of gland duct regions S are displayed in a color-coded manner according to the shape feature amount.

Figure 13:
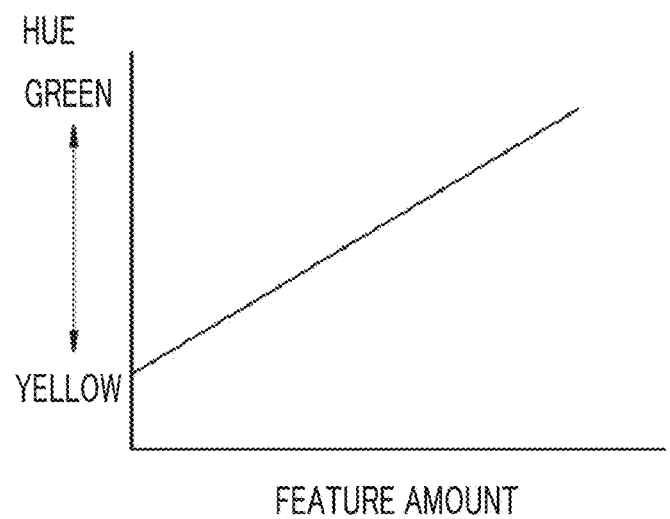
FIG. 13 is a graph of an example in which a color is continuously changed with respect to a change in feature amount.
Figure 14:
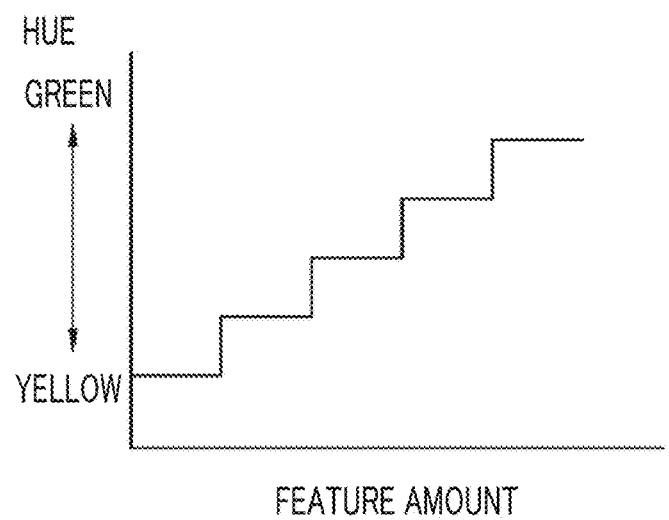
FIG. 14 is a graph of an example in which a color is changed stepwise with respect to a change in feature amount.

As a method in which the color assignment unit 76 assigns a color to the blood vessel region V or the gland duct region S, the color may be continuously changed with respect to a change in the feature amount as shown in FIG. 13, or the color may be changed stepwise with respect to a change in the feature amount as shown in FIG. 14. Although the relationship between the feature amount and the hue, such as green or yellow, is described as an example in FIGS. 13 and 14, the same applies to the relationship between the brightness or saturation and the feature amount. In the case of using the color assignment tables 87 and 88 for blood vessels or gland ducts, the color assignment tables 87 and 88 are set so as to satisfy the relationship shown in FIG. 13 or 14.

Instead of using the color assignment tables 87 and 88, the color assignment unit 76 may use a function of converting the feature amount into color.

In this example, a warm color system of red, yellow, brown, and the like is used as colors assigned to the blood vessel region V of the blood vessel region image 84, and a cold color system of blue, violet, and the like is used as colors assigned to the gland duct region S of the gland duct region image 86.

In FIG. 5, the image combining unit 78 generates a first composite image 92 by superimposing the pseudo-color blood vessel region image 89 on the reduced original image 83 so as to be combined with each other using the reduced original image 83 as a base image. In addition, the image combining unit 78 generates a second composite image 93 by superimposing the pseudo-color gland duct region image 91 on the reduced original image 83 so as to be combined with each other using the reduced original image 83 as a base image. The special image processing unit 64 output the first composite image 92 and the second composite image 93 to the display control unit 65 as special images.

Figure 15:
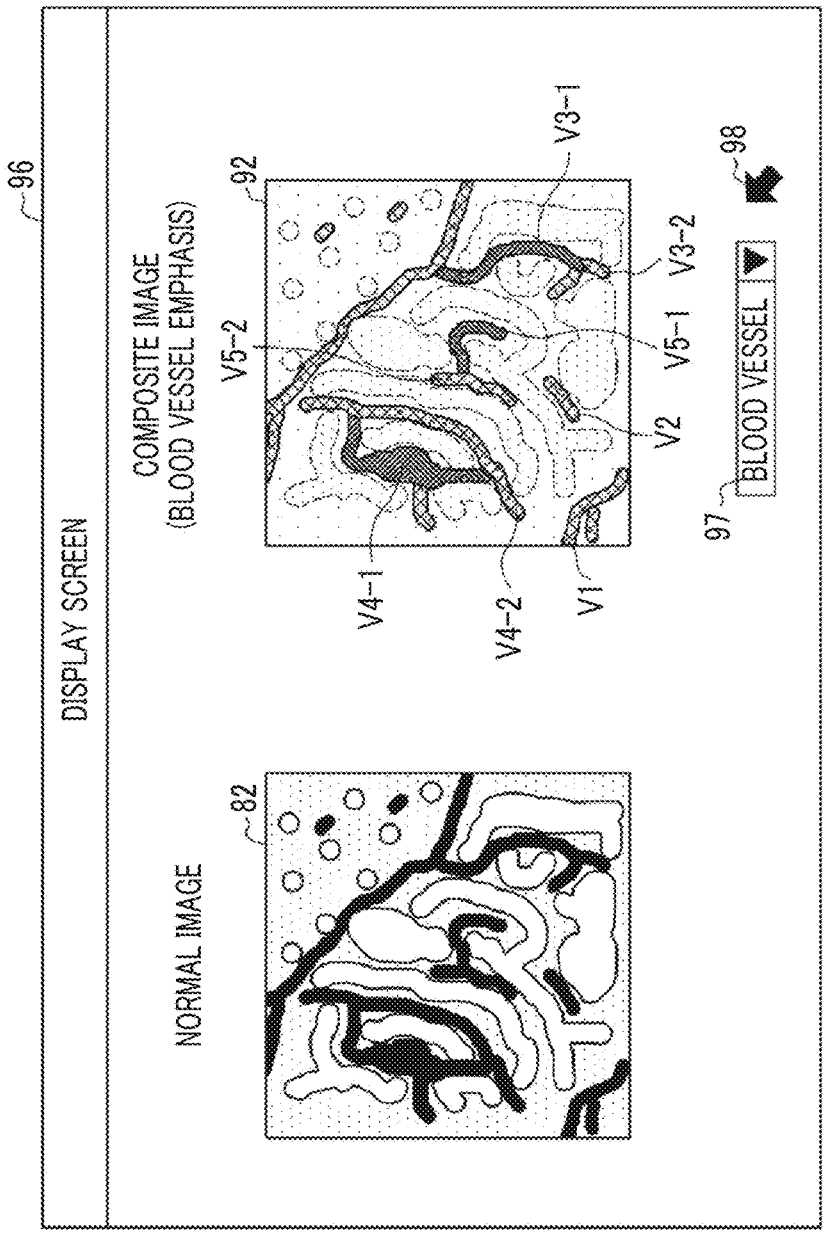
FIG. 15 is an explanatory diagram of a display screen of a composite image in which a blood vessel region is emphasized.
Figure 16:
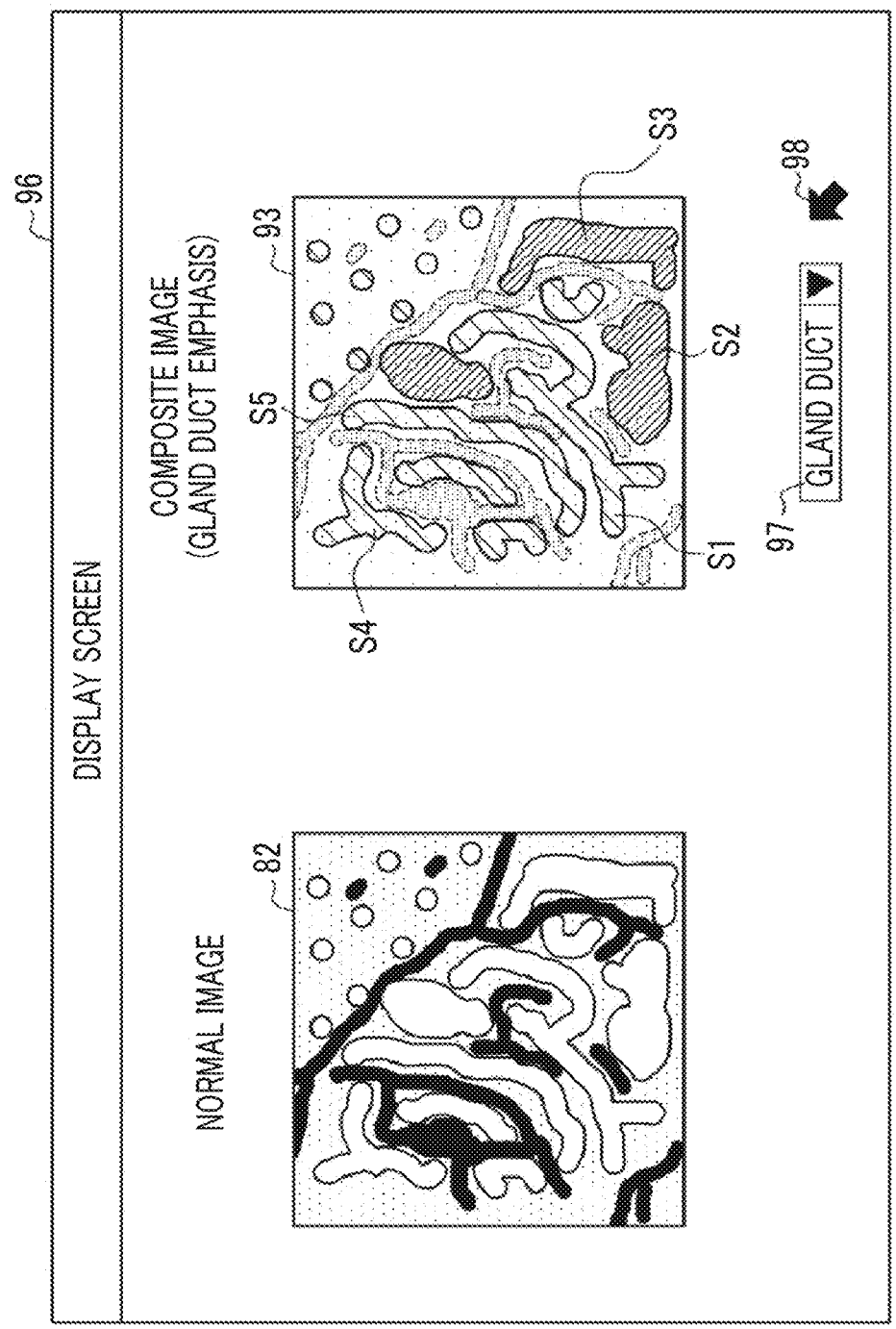
FIG. 16 is an explanatory diagram of a display screen of a composite image in which a gland duct region is emphasized.

As shown in FIGS. 15 and 16, the display control unit 65 generates a display screen 96 to display the original image 82, which is a normal image, and the first composite image 92 and the second composite image 93, which are special images, in parallel, and displays the display screen 96 on the monitor 18. On the display screen 96, a selection box 97 is provided as a selection operation portion for selecting which of the first composite image 92 and the second composite image 93 is to be displayed. The selection box 97 is operated by a pointer 98, such as a mouse.

As shown in FIG. 15, in a case where blood vessel is selected in the selection box 97, the first composite image 92 in which the blood vessel region V is emphasized is displayed. As shown in FIG. 16, in a case where gland duct is selected, the second composite image 93 in which the gland duct region S is emphasized is displayed. It is also possible to switch the display by operating the selection box 97 during the examination.

In addition to displaying the original image 82 and the composite image 92 and 93 in parallel as on the display screen 96 shown in FIGS. 15 and 16, each image of the original image 82 and the composite image 92 and 93 may be selectively displayed frame by frame.

Figure 17:
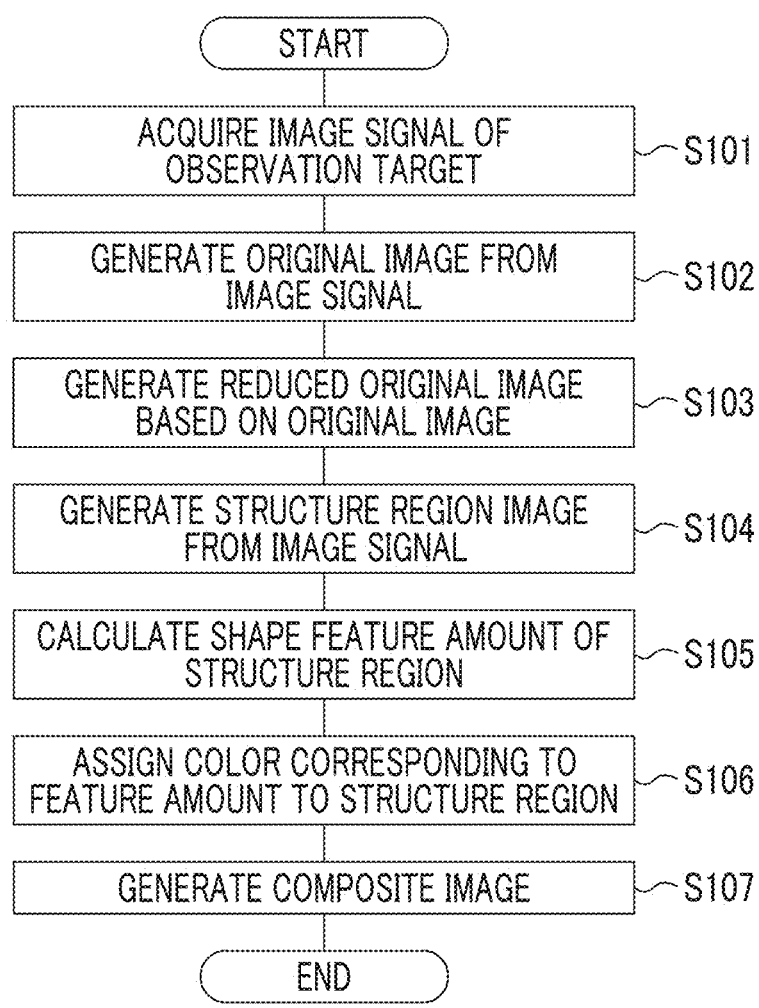
FIG. 17 is a flowchart showing a special image processing procedure.

The operation of the above configuration will be described with reference to a flowchart shown in FIG. 17. In a case where the endoscope 12 is connected to the light source device 14 and the processor device 16 to start the endoscope system 10, the imaging sensor 48 of the endoscope 12 starts imaging. In the light source device 14, the LEDs 20a to 20d of four colors of V, B, G, and R are turned on, and white light based on the mixing of light beams of four colors is supplied to the endoscope 12 as illumination light.

In a case where the insertion unit 12a of the endoscope 12 is inserted into the body of a patient or the like, illumination light is emitted to an observation target in the body through the light guide 41, and reflected light that is reflected from the observation target is incident on the imaging sensor 48. The imaging sensor 48 images the observation target in the body under the illumination light, and RGB image signals of the observation target are input to the processor device 16. In the initial setting, the endoscope system 10 is started in the normal observation mode. In the processor device 16, the normal image processing unit 62 acquires the RGB image signals, and generates a normal image in which the observation target is drawn in color based on the acquired image signals. The normal image is input to the display control unit 65, and the display control unit 65 displays the display screen 96, which displays the normal image, on the monitor 18.

In a case where the mode selector SW 13a is operated by the operation of a doctor, the signal input path is switched by the image processing switching unit 60, and the endoscope system 10 switches from the normal observation mode to the special observation mode. The special image processing unit 64 acquires the RGB image signals of the observation target (step (S) 101). Then, the original image generation unit 68 generates the original image 82 similar to the normal image based on the RGB image signals (S102). The reduced original image generation unit 70 generates the reduced original image 83 having reduced color and contrast by monochromatically transforming the color original image 82 (S103).

The structure region image generation unit 72 generates the blood vessel region image 84 based on the B image signal, and generates the gland duct region image 86 based on the G image signal (S104). Then, the feature amount calculation unit 74 calculates the shape feature amount of each of the blood vessel region V and the gland duct region S based on the structure region image of each of the blood vessel region image 84 and the gland duct region image 86 (S105).

As shown in FIGS. 6 to 8, the feature amount calculation unit 74 calculates the feature amount for each blood vessel region V and each gland duct region S in the blood vessel region image 84 and the gland duct region image 86. As shown in FIG. 7, in a case where one blood vessel region V or one gland duct region S is divided into a plurality of regions, the feature amount is calculated for each region.

The color assignment unit 76 assigns a color corresponding to the feature amount for each region, for which the feature amount has been calculated, for the blood vessel region V in the blood vessel region image 84 or the gland duct region S in the gland duct region image 86 using the color assignment tables 87 and 88 as shown in FIGS. 9 to 12 (S106).

For example, as shown in FIG. 6, in a case where the feature amount is calculated for the entire one blood vessel region V2 in the blood vessel region image 84, the entire blood vessel region V2 is colored with a color assigned corresponding to the calculated feature amount. In addition, as shown in FIG. 7, in a case where one blood vessel region V5 is divided into a plurality of regions V5-1 and V5-2 and the feature amount is calculated for each of the divided regions V5-1 and V5-2, each of the divided regions V5-1 and V5-2 is colored with a color assigned corresponding to the calculated feature amount. Also for the gland duct region S of the gland duct region image 86, color assignment is performed using the same method.

In this example, the color assignment unit 76 assigns colors of different systems to respective structure regions by using the warm color system of red, yellow, brown, and the like for the blood vessel region V of the blood vessel region image 84 and the cold color system of blue, violet, and the like for the gland duct region S of the gland duct region image 86. In this manner, the pseudo-color blood vessel region image 89 and the pseudo-color gland duct region image 91 are generated (refer to FIG. 5).

The image combining unit 78 generates the first composite image 92 by superimposing the pseudo-color blood vessel region image 89 on the reduced original image 83, and generates the second composite image 93 by superimposing the pseudo-color gland duct region image 91 on the reduced original image 83 (S107).

As shown in FIGS. 15 and 16, the first composite image 92 or the second composite image 93 is displayed on the display screen 96 together with the original image 82 that is a normal image. The first composite image 92 and the second composite image 93 are switched by selection of the selection box 97. The doctor can observe a desired image by operating the selection box 97.

The pseudo-color blood vessel region image 89 and the pseudo-color gland duct region image 91, which are used as the first composite image 92 and the second composite image 93, are color-coded according to the shape feature amount of the blood vessel region V or the gland duct region S. As a result, it is possible to easily distinguish a plurality of structure regions having different shape feature amounts from each other. It is very useful in lesion diagnosis to distinguish regions having different shape feature amounts from each other.

For example, in a lesion region where a tumor or the like is generated and a normal region, the shape features of structures, such as the widths or running states of blood vessels and the sizes of gland ducts, are largely different. Since the doctor makes a diagnosis focusing on such a shape feature, a lesion region and a normal region can be easily distinguished if regions having different shape features can be easily distinguished. Also in the lesion region, the running state of a blood vessel, the shape of a gland duct structure, and the like change depending on the location. Since a color can be assigned to each blood vessel region or each gland duct region according to the shape of the region, it is easy to visually grasp regions having different feature amounts.

In this example, the reduced original image 83 is used as a base image in which such pseudo-color blood vessel region image 89 and pseudo-color gland duct region image 91 are superimposed. As described above, the reduced original image 83 is a monochrome gray scale image in which the color and the contrast of the original image 82 are reduced. In the pseudo-color blood vessel region image 89 and the pseudo-color gland duct region image 91, the blood vessel region V and the gland duct region S are emphasized, but other information is discarded.

In contrast, the reduced original image 83 is a monochrome image, but the information of the observation target discarded in the pseudo-color blood vessel region image 89 or the pseudo-color gland duct region image 91 is drawn. Therefore, it is possible to grasp the overall characteristics of the observation target. For example, since the pseudo-color blood vessel region image 89 and the reduced original image 83 are superimposed to form the first composite image 92, the blood vessel region V is color-coded and highlighted. In addition, in the reduced original image 83, not only the blood vessel region V but also the gland duct region S and the like are drawn. Therefore, it is possible to observe the color-coded blood vessel region V while grasping the overall characteristics of the observation target.

In particular, in this example, since the reduced original image 83 is not a binary image but a gray scale image having a predetermined number of gradations, it is possible to clearly grasp the overall characteristics of the observation target compared with a binary image.

In this example, the common reduced original image 83 is used as base images of both the first composite image 92 and the second composite image 93. Since the common reduced original image 83 is used, the difference between structure regions (the blood vessel region V and the gland duct region S) emphasized in each of the first composite image 92 and the second composite image 93 becomes clear. Therefore, it is easy to compare both the images with each other.

The reduced original image 83 used as base images of the first and second composite images 92 and 93 is a monochrome image, the degree of freedom of color assignment in the pseudo-color blood vessel region image 89 or the pseudo-color gland duct region image 91 is high. That is, in a case where the original image 82 is used as a base image, the same color as the color used in the original image 82 cannot be used as the assignment color of the pseudo color. For this reason, there are many restrictions on colors that can be used. In contrast, by using the reduced original image 83 whose number of colors is reduced by monochromatization as a base image, it is possible to increase the number of colors that can be used. As a result, detailed color-coding is possible according to the feature amount. As the number of colors that can be used becomes larger, fine differences in shape feature amounts can be expressed in colors more easily.

As shown in FIG. 13, by continuously changing the color to be assigned according to the feature amount change, it is possible to express small changes in shape features with gradation. Therefore, it is easy to visually grasp minute changes in feature amounts.

In this example, different colors is assigned to different structure region images, such as using the warm color system of red, yellow, brown, and the like as colors assigned to the blood vessel region V of the blood vessel region image 84 and using the cold color system of blue, violet, and the like as colors assigned to the gland duct region S of the gland duct region image 86. In this manner, by using different colors according to the types of structure regions, such as the blood vessel region V and the gland duct region S, it is possible to obtain an effect that it is easy to distinguish the types of structure regions from each other.

In this example, colors of the warm color system and the cold color system have been described as examples of different colors for respective structure regions. Here, different colors include all cases where at least one of hue, brightness, or saturation is different. However, among hue, brightness, and saturation, it is considered that the hue can easily give visually different impressions. Therefore, it is preferable to assign colors with different hues to respective structure regions. Even in a case where colors with different hues are used, it is more preferable to use colors of different systems, such as a warm color system and a cold color system in this example. This is because the warm color system and the cold color system have relatively distant positions in the hue circle as in the complementary color relationship and accordingly visually different impressions are more easily given.

In this example, a warm color system is used for the blood vessel region image 84 and the cold color system is used for the gland duct region image 86 so that it is easy to distinguish the images from each other. In addition, in each of the blood vessel region image 84 and the gland duct region image 86, the color is changed according to the feature amount within similar colors of the warm color system or the cold color system. Therefore, it is possible to keep the unity of color for each type of structure region. In addition, for the same type of structure region, different colors are assigned according to the shape feature amount within similar colors. As a result, regions having different feature amounts are also color-coded. Here, the similar colors refer to colors whose positions in the hue circle are included in the range of about 120°, for example, red and orange or green and yellowish green in the hue circle.

Second Embodiment

Figure 18:
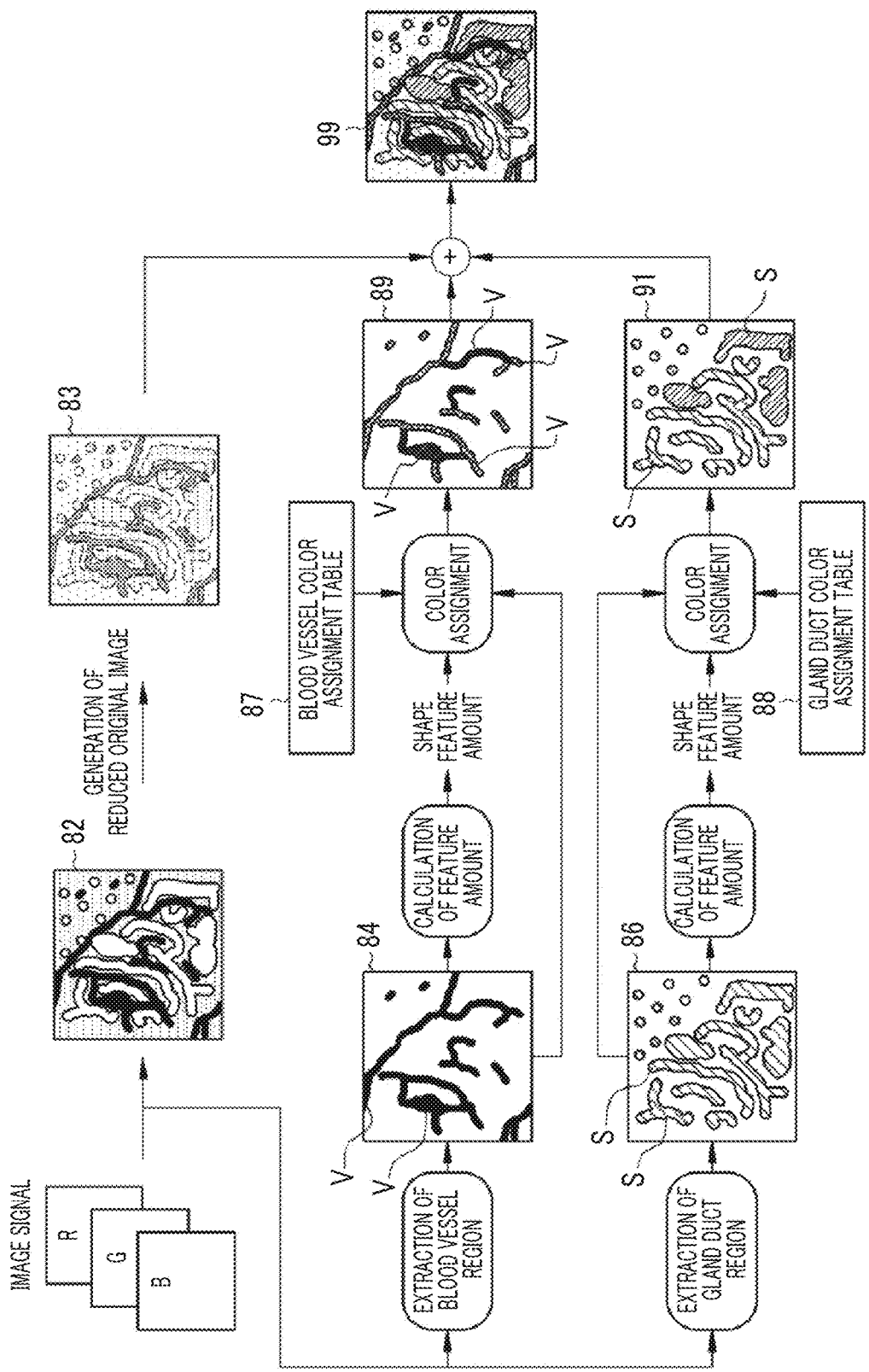
FIG. 18 is an explanatory diagram of special image processing in a second embodiment.
Figure 19:
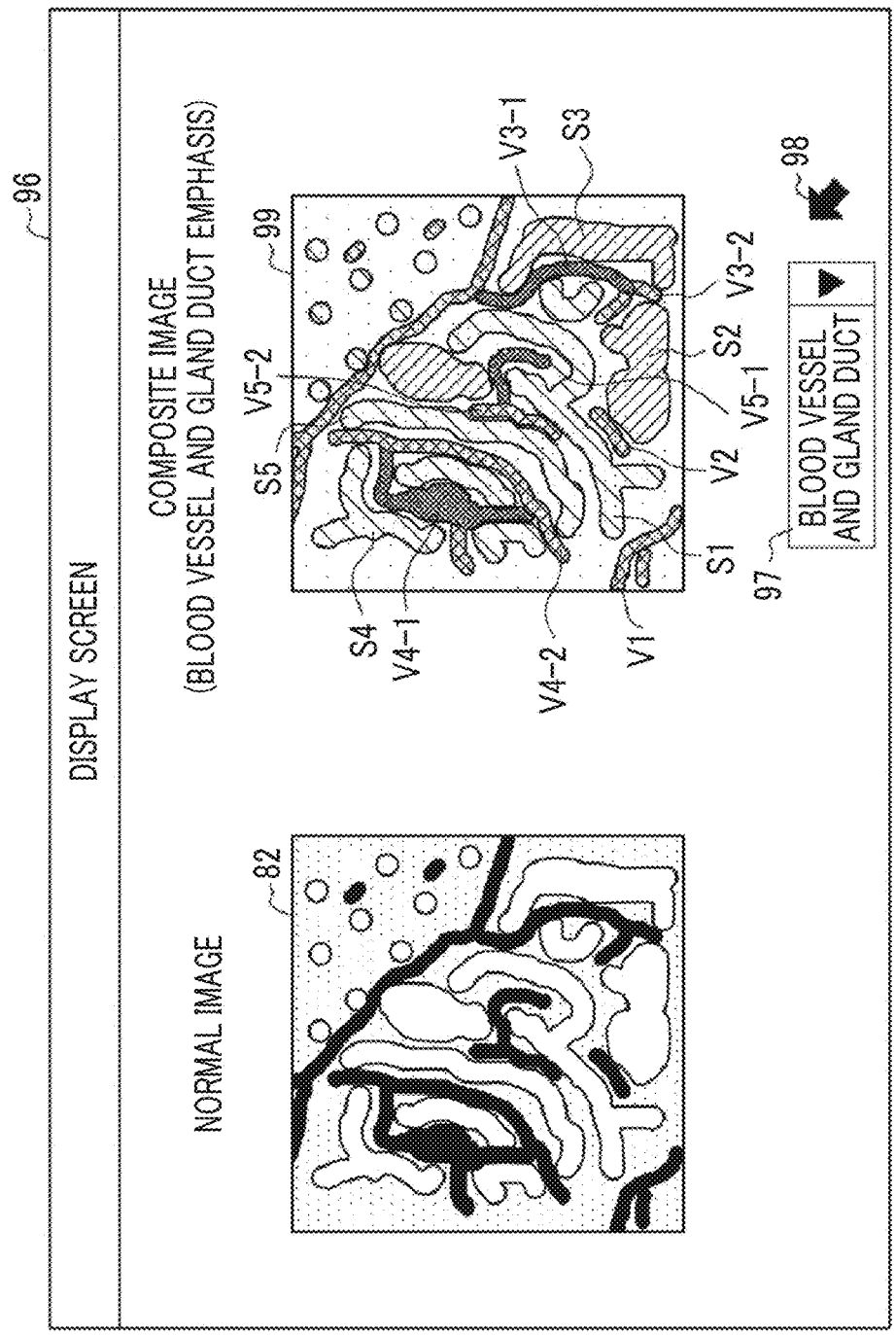
FIG. 19 is an explanatory diagram of a display screen of a composite image in the second embodiment.

As in a second embodiment shown in FIGS. 18 and 19, the image combining unit 78 may generate one third composite image 99 by superimposing both the pseudo-color blood vessel region image 89, in which the blood vessel region V is color-coded, and the pseudo-color gland duct region image 91, in which the gland duct region S is color-coded, on the reduced original image 83. As shown in FIG. 19, on the display screen 96, the third composite image 99 is displayed in parallel with the original image 82. According to this, a plurality of structure regions color-coded according to the feature amount can be observed within the one third composite image 99. The original image 82 and the third composite image 99 may be selectively displayed frame by frame.

In addition, the display forms shown in FIGS. 15 and 16 of the first embodiment and the display form shown in FIG. 19 may be switched by the selection box 97. In this manner, the first composite image 92, the second composite image 93, and the third composite image 99 can be switched to be selectively displayed on the one display screen 96. Needless to say, a plurality of composite image 92, 93, and 99 may be displayed in parallel within the display screen 96.

Third Embodiment

Figure 20:
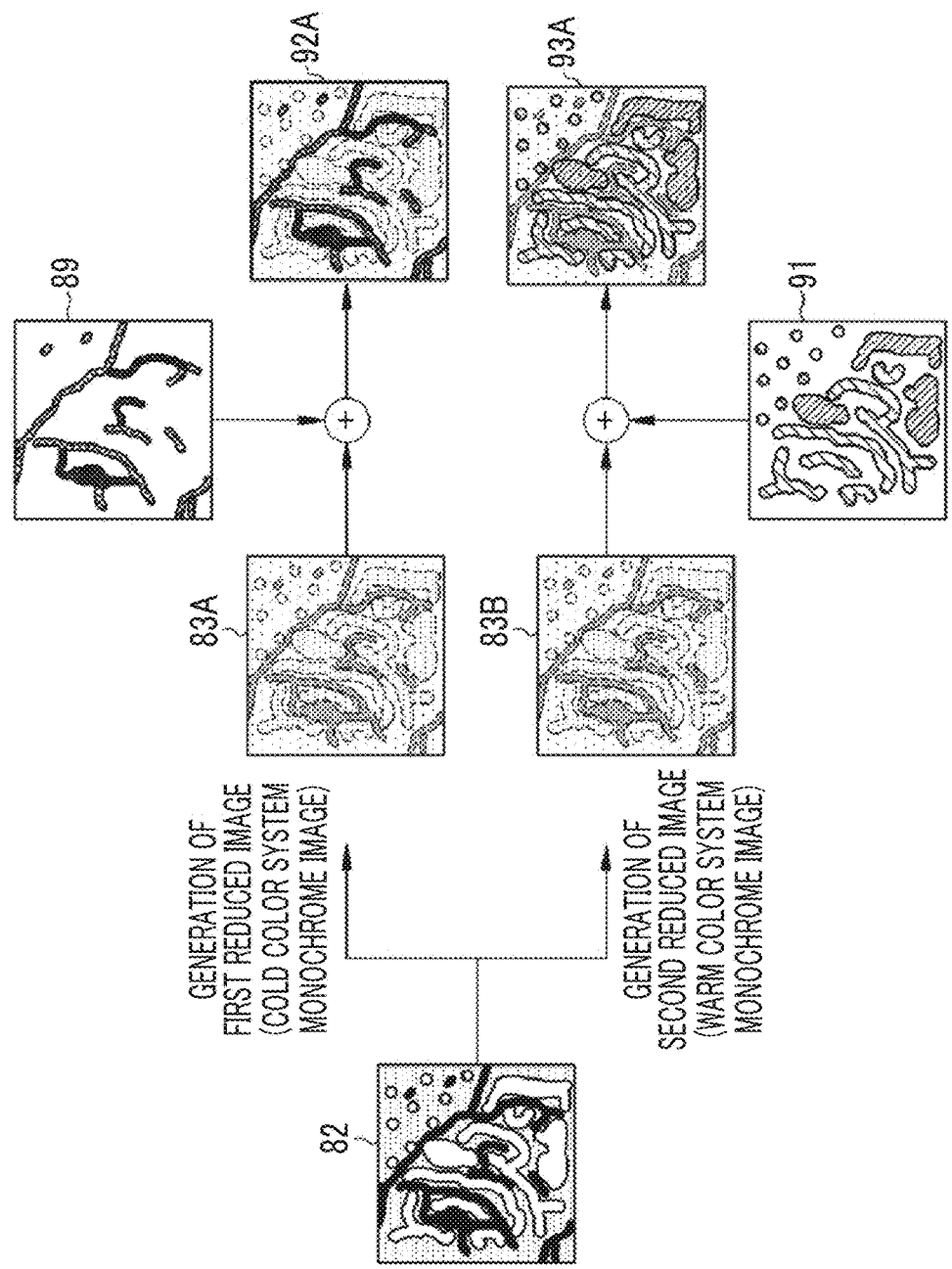
FIG. 20 is an explanatory diagram of special image processing in a third embodiment.

As in a third embodiment shown in FIG. 20, a base image to be used for each type of structure region image may be a different reduced original image. In the example shown in FIG. 20, a first reduced original image 83A is used as a base image to be combined with the pseudo-color blood vessel region image 89, and a first composite image 92A is generated. A second reduced original image 83B is used as a base image to be combined with the pseudo-color gland duct region image 91, and a second composite image 93A is generated.

For example, although both the first reduced original image 83A and the second reduced original image 83B are monochrome gray scale images, but the colors used are different. Specifically, the first reduced original image 83A is a monochrome gray scale image of blue and white of the cold color system, and the second reduced original image 83B is a monochrome gray scale image of red and white of the warm color system.

As shown in the first embodiment, the color of the warm color system is assigned to the pseudo-color blood vessel region image 89. Therefore, the color of the warm color system assigned to the blood vessel region V to be emphasized can be made noticeable by using the first reduced original image 83A, in which the color of the cold color system is used, as a base image. On the contrary, the color of the cold color system is assigned to the pseudo-color gland duct region image 91. Therefore, the color of the cold color system assigned to the gland duct region S to be emphasized can be made noticeable by using the second reduced original image 83B, in which the color of the warm color system is used, as a base image.

In this example, the color to be used is changed between the first reduced original image 83A and the second reduced original image 83B. However, the sharpness may be changed instead of changing the color. For example, soft focus processing is performed on the first reduced original image 83A that is the background of the pseudo-color blood vessel region image 89, so that the target to be drawn is blurred. Since the blood vessel region V is relatively thin, it is possible to emphasize the blood vessel region V by blurring the background. Sharpness change and color change may be combined.

By changing the reduced original image 83 to be used as a base image according to the type of the structure region image as described above, it is possible to use the appropriate reduced original image 83 according to the type of the structure region image.

Fourth Embodiment

Figure 21:
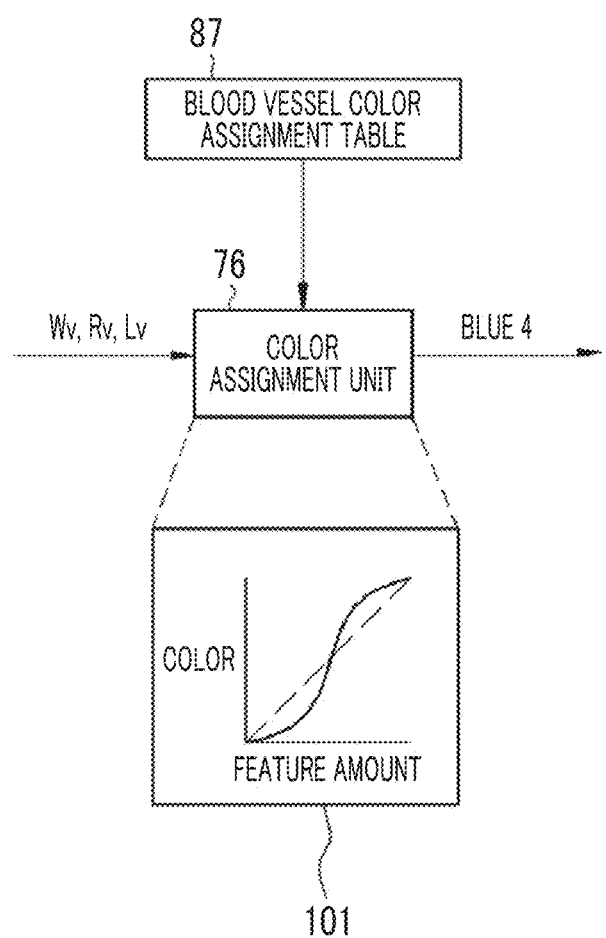
FIG. 21 is an explanatory diagram of color assignment processing using gamma conversion.

As in a fourth embodiment shown in FIG. 21, in a case where the color assignment unit 76 determines a position based on three feature amounts (Wv, Rv, Lv) on the color space of the blood vessel color assignment table 87, gamma conversion may be performed. A gamma curve 101 shows a correspondence relationship between a feature amount that is an input value and a position on the color space that is an output value. By changing the gamma curve 101, it is possible to increase the color resolution in a specific range of the input value or conversely reduce the color resolution. Thus, for example, for a specific input range of the feature amount, it is possible to express small changes in the feature amount by large color changes.

Fifth Embodiment

Figure 22:
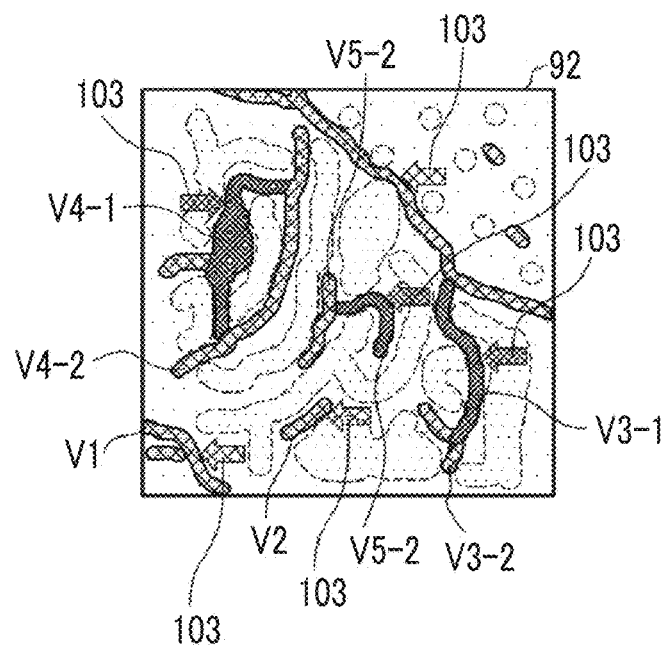
FIG. 22 is an explanatory diagram of a display form in which color-coded marks are used.

In the embodiments described above, as a color assignment method for the blood vessel region V or the gland duct region S for which the feature amount has been calculated, a method of coloring each region itself of the blood vessel region V or the gland duct region S by painting has been described as an example. However, as in a fifth embodiment shown in FIG. 22, colors may be assigned using a mark 103 indicating a color.

Figure 23:
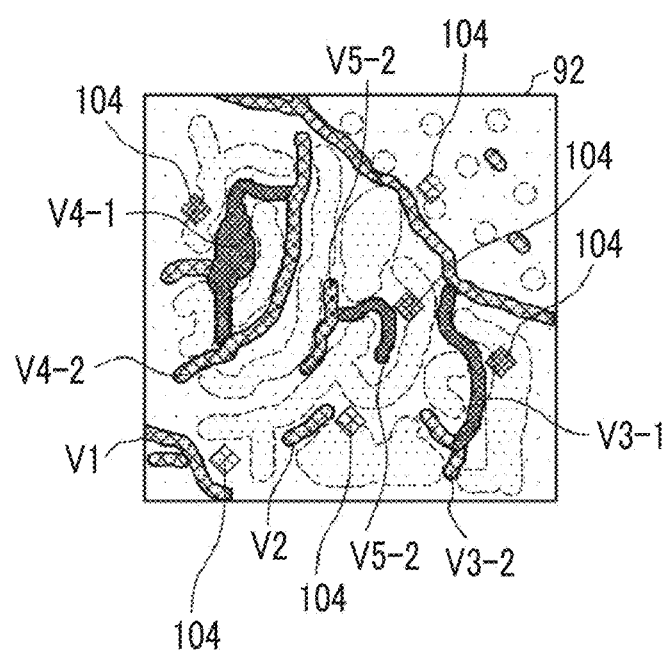
FIG. 23 is an explanatory diagram of a display form in which marks having shapes different from those in FIG. 22 are used.

In the image, the mark 103 is colored with a color corresponding to the calculated feature amount, and is inserted at a position near the region for which the feature amount has been calculated. Even in this manner, it is possible to distinguish between regions having different feature amounts by color. For the region itself for which the feature amount has been calculated, such as the blood vessel region V, coloring may or may not be performed. The mark 103 has an arrow shape. An example of the mark 103 may be other than an arrow shape. For example, as shown in FIG. 23, a rhombic mark 104 may be used. It is needless to say that a circular shape and a polygonal shape may be used. Animation display may be performed by using a method of blinking or rotating the marks 103 and 104. Since a dynamic visual effect can be given by the animation display, a strong impression can be given.

Sixth Embodiment

Figure 24:
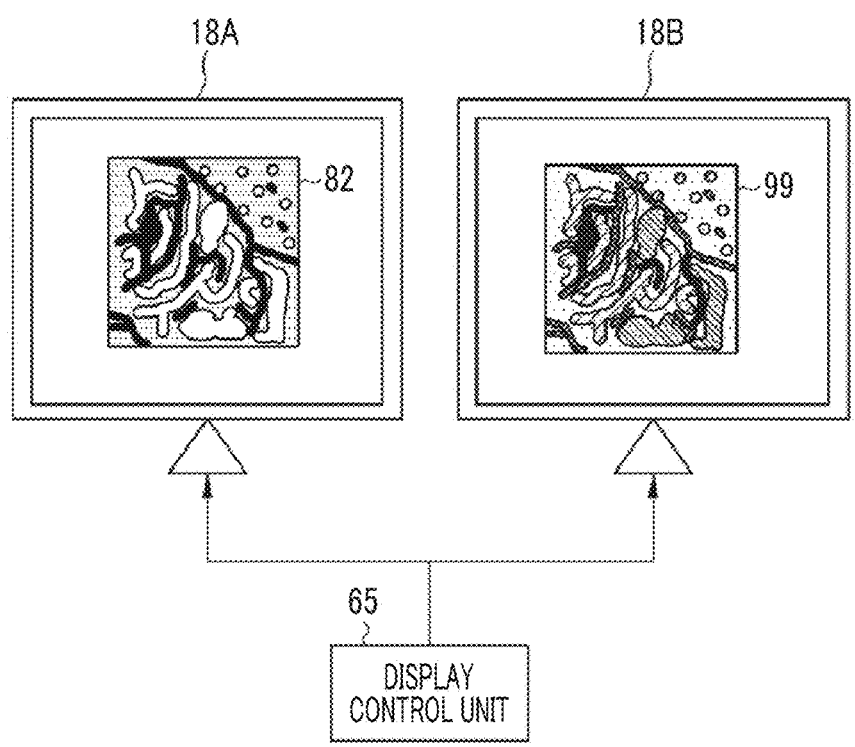
FIG. 24 is an explanatory diagram of a form in which a multi-monitor is used.

As in a sixth embodiment shown in FIG. 24, the display control unit 65 may be able to output the display screen to a multi-monitor. For example, the display control unit 65 outputs a display screen, which is for displaying the original image 82 that is a normal image, and a display screen, which is for displaying the composite image 99 that is a special image, to a plurality of monitors 18A and 18B. Since the screen size can be increased by using the multi-monitor, observation can be performed with a large image.

In each of the embodiments described above, an example has been described in which the reduced original image 83 is generated by performing processing for reducing both the color and the contrast of the original image 82. However, only one of the color and the contrast may be reduced. In a case where only the contrast is reduced, colors remain in the reduced original image 83, but the color of the background becomes less noticeable due to the contrast reduction. Therefore, even if a pseudo-color structure region image is superimposed on the background, the color of the background is unlikely to have an adverse effect on the visibility of the color-coded structure region image. For this reason, compared with a case in which the contrast is not reduced, it is possible to secure the degree of freedom of color assignment according to the shape feature of the structure. Needless to say, it is more preferable to combine the contrast reduction with the color reduction instead of the contrast reduction.

The method of reducing the color may be other than monochromatization, and any method may be used as long as the number of colors is limited compared with a color image.

In each of the embodiments described above, the blood vessel region V and the gland duct region S have been described as examples of a structure region to be emphasized. However, structure regions other than these may be emphasized. For example, there are a reddened region of a mucosa, a discolored region (brownish region), and a foreign matter region, such as a polyp. In addition to the examples shown in the embodiments described above, the shape feature amount may be, for example, the area of a region, a boundary length, the length of the main axis, an approximation rate for a predetermined shape, the density of a plurality of regions, or a value calculated according to the combination of the plurality of feature amounts.

As a method of calculating the feature amount, for example, a method of preparing a predetermined basic pattern and calculating the similarity with the basic pattern as a feature amount may be used. For example, as basic patterns, a plurality of types of typical patterns of lesions, such as "regular dot shape" and "margin unclear", are prepared. By comparing such a plurality of basic patterns with the structure region, the similarity for each basic pattern is calculated as a shape feature amount. Then, a basic pattern with the highest similarity among the calculated similarities is determined as a pattern of the structure region. In the structure region, color assignment is performed for each determined pattern.

In a case where the similarity between the structure region and the basic pattern is calculated as the feature amount as described above, the feature amount may be calculated for the entire certain region including a plurality of structure regions instead of calculating the feature amount separately for each structure region in the structure region as in the embodiments described above. Specifically, it is determined that the entire certain region including a plurality of structure regions is similar to, for example, "regular dot shape", and a color corresponding to "regular dot shape" is assigned to the entire region. In this case, a legend showing the correspondence relationship between the basic pattern and the color, such as "regular dot shape" is "blue 1", may be displayed within the display screen 96.

In the embodiments described above, a structure region image, such as a blood vessel region image or a gland duct region image, is generated for each type of structure. However, a structure region image including a plurality of types of structure regions may be generated. Needless to say, it is preferable to generate a structure region image for each type of structure as in the embodiments described above since structures can be clearly distinguished from each other.

In the above embodiments, an example has been described in which a composite image, in which a structure region is emphasized, is generated and displayed during video imaging. However, the composite image in which a structure region is emphasized may be generated and displayed based on a still image captured at the time of still image capturing. Alternatively, the composite image generation and display may be performed at both the time of video imaging and the time of still image capturing.

Although the example in which the mode selector SW for switching to the special observation mode is provided in the operation unit of the endoscope 12 has described, various operation units, such as a foot switch, a mouse, a keyboard, and a touch panel display, may be made to function as the mode selector SW. Alternatively, a line-of-sight detection sensor for detecting the line-of-sight of a doctor or a motion sensor for detecting the movement of a hand or a foot may be provided so as to function as the mode selector SW. In addition, a switch that operates by voice recognition or an electroencephalogram detection switch may be used.

Instead of switching by the mode selector SW, the observation mode may be automatically changed at predetermined time intervals. This is convenient since the operation of the doctor is not necessary. As a form of the monitor, in addition to the stationary monitor, a head mounted display may be used so that a composite image is displayed on the head mounted display.

In the above embodiments, as a method of extracting a structure region, an example has been described in which the B image signal or the G image signal among image signals captured with white light is used. However, instead of a single-color image signal, the color original image 82 captured under white light may be used. In this case, as described below, blood vessels to be extracted can be selected according to the color of a blood vessel.

It is known that there is a correlation between the wavelength of light and the degree of penetration into the mucosa. Specifically, the degree of penetration of light into the mucosa becomes lower as the wavelength becomes shorter, and the degree of penetration of light into the mucosa becomes higher as the wavelength becomes longer. Therefore, in a case where the mucosa is imaged under white light, the color changes with the depth of the blood vessel. For example, in the case of blood vessels in the surface layer, the amount of arrival of blue light is large, and the blue light is absorbed in blood. Therefore, since the reflected light has a small amount of blue component, the blood vessels in the surface layer are drawn in red in the captured image. In contrast, in the case of blood vessels in the deep layer, the amount of arrival of blue light is small, and the blue light is reflected within the mucosa. Therefore, since the reflected light has a large amount of blue component, the blood vessels in the deep layer are drawn in a color close to violet in the captured image. Blood vessels in the middle layer are drawn in brown.

In this manner, since the color of the blood vessel region changes with a depth within the mucosa, a blood vessel region at a specific depth can be extracted by selecting the color of a blood vessel region to be extracted, such as red for the surface layer, brown for the middle layer, and violet for the deep layer, in the extraction processing. A plurality of blood vessel regions at different depths extracted as described above may be color-coded, so that the blood vessel regions can be distinguished from each other in the composite image.

Instead of an image signal obtained under white light, a narrowband image signal obtained under special light, for example, narrowband light having a narrow band of a part of each wavelength range of blue light, green light, and red light as a wavelength band. By using narrowband light (blue narrowband light or green narrowband light) that matches a band in which the absorption rate of hemoglobin in blood is high, it is possible to obtain an image signal in which the blood vessel region is drawn in a state of higher contrast.

Even in a case where blue narrowband light and green narrowband light are used, the color changes with the depth of the blood vessel as in the case of white light. Specifically, blood vessels in the surface layer are red, blood vessels in the middle layer are brown, and blood vessels in the deep layer are bluish green. Even in a case where narrowband light beams of a plurality of colors, since the color changes with the depth of the blood vessel, it is possible to extract a blood vessel region at a specific depth by color.

Alternatively, an image signal obtained under light other than the normal visible light, for example, special light using infrared light or ultraviolet light may be used. Using an agent that emits fluorescence that is selectively accumulated in a lesion part, an image signal obtained by receiving the fluorescence emitted in the case of emitting infrared light, ultraviolet light, or special light having a specific wavelength may be used. Since fluorescence emits light having a specific wavelength, it is possible to extract a light emitting region showing a lesion by color.

Alternatively, an image signal obtained by imaging in a state in which a dyeing solution, such as an indigo carmine solution, a crystal violet solution, and an iodine diluent, is sprayed into the digestive tract may be used.

In the case of acquiring an image signal with special light as described above, it is necessary to change the illumination light between the normal observation mode and the special observation mode. For example, the light source control unit 21 changes the illumination light between the normal observation mode and the special observation mode by turning on and off the violet light V, the blue light B, the green light G, and the red light R and further by changing the light amount ratio. The normal observation mode and the special observation mode may be automatically changed at predetermined time intervals. In a case where the dyeing solution is sprayed, since the contrast of a specific structure is emphasized by the color of the dyeing solution, it is preferable to switch the illumination light for each dyeing solution.

As pre-processing for extracting a structure region, it is preferable to perform the following processing. In the case of extracting a structure region from the B image signal, first, a bright spot causing halation is searched for in the B image signal as an extraction source, and a region including its surroundings is excluded from extraction targets. A region having a brightness equal to or less than a predetermined threshold value is also excluded from extraction targets. This is because, in a region to be excluded, no blood vessel is drawn or it is not possible to distinguish blood vessels from other regions even if the blood vessels are not drawn, and accordingly, extraction is difficult.

In a case where the original image 82 is used as an image that is a structure region extraction source, a region where a treatment tool appears may be further excluded from extraction targets in the original image 82. Since various treatment tools, such as biopsy forceps, clipping treatment tools, and snares, are used in the procedure of the endoscope, such treatment tools may appear in a captured image.

In a region where a treatment tool appears, since the observation target becomes a shadow of the treatment tool, it is preferable to exclude such a region. The treatment tool has a distal end portion formed of metal and a guide sheath extending toward the proximal end side that is formed of white resin. A coil sheath is formed of metal. Therefore, since the approximate color of the treatment tool is fixed, regions having these colors may be determined to be exclusion target regions and excluded from the original image 82.

In a case where only a small amount of extraction target region excluding the exclusion target region remains, for example, the extraction target region excluding the exclusion target region is equal to or less than 10% of the entire image, the image may be excluded from images from which a structure region is to be extracted (extraction processing may not be performed on the image). Since such an image has few extraction target regions, almost no structure region is extracted, and the processing is useless.

In the embodiments described above, LEDs of four colors of the violet light V, the blue light B, the green light G, and the red light R are used as light sources. However, LEDs of three colors of B, G, and R may be used. Instead of the LED, other semiconductor light sources such as electro luminescence (EL) may be used in addition to the laser diode (LD) described above. Alternatively, a white light source, such as a xenon lamp, may be used.

An example has been described in which a color imaging sensor having BGR micro filters corresponding to pixels on the imaging surface is used as an imaging sensor. However, a monochrome imaging sensor may be used. In a case where a monochrome imaging sensor and a white light source, such as a xenon lamp, are combined, a rotary filter for separating the light of the xenon lamp into light beams of BGR is provided.

In the above embodiments, an example has been described in which the processor device directly connected to the endoscope is made to function as the image processing apparatus of the present invention. However, the image processing apparatus may be an apparatus independent from the processor device.

The present invention can be applied to various types of medical image processing apparatuses in addition to the processor device built into the capsule endoscope system. The present invention extends to an image processing program causing a computer to function as an image processing apparatus or a storage medium storing an image processing program in addition to the image processing apparatus and method.

EXPLANATION OF REFERENCES

10: endoscope system
16: processor device
65: display control unit
68: original image generation unit
70: reduced original image generation unit
72: structure region image generation unit
74: feature amount calculation unit
76: color assignment unit
78: image combining unit
82: original image
83: reduced original image
84: blood vessel region image
86: gland duct region image
87: blood vessel color assignment table
88: gland duct color assignment table
89: pseudo-color blood vessel region image
91: pseudo-color gland duct region image
92, 93, 99: composite image
96 display screen

What is claimed is:
1. An image processing apparatus, comprising:
   an image signal acquisition unit that acquires an image signal obtained by imaging an observation target in a living body;
   an original image generation unit that generates an original image in which the observation target is drawn in color based on the image signal;

a reduced original image generation unit that generates a reduced original image by performing processing for reducing at least one of a color or a contrast on the original image;
a structure region image generation unit that generates a structure region image in which one or more structure regions are extracted from the acquired image signal;
a feature amount calculation unit that calculates a shape feature amount of the structure region based on the structure region image;
a color assignment unit that assigns a color corresponding to the feature amount to the structure region; and
an image combining unit that generates a composite image by superimposing the reduced original image and the structure region image subjected to the color assignment,
wherein the structure region image generation unit generates a first structure region image showing a first structure region and a second structure region image showing a second structure region,
wherein the reduced original image generation unit generates a first reduced original image and a second reduced original image, and
wherein the image combining unit generates, as the composite image, a first composite image obtained by combining the first structure region image and the first reduced original image and a second composite image obtained by combining the second structure region image and the second reduced original image.

2. The image processing apparatus according to claim 1, wherein the color assignment unit changes a color assigned to the structure region stepwise or continuously according to the feature amount.

3. The image processing apparatus according to claim 1, wherein the color assignment unit assigns different colors to the first structure region image and the second structure region image.

4. The image processing apparatus according to claim 1, wherein the image combining unit generates, as the composite image, a third composite image obtained by combining three images of the first structure region image, the second structure region image, and the reduced original image.

5. The image processing apparatus according to claim 1, wherein the image combining unit uses the reduced original image common to the first composite image and the second composite image.

6. The image processing apparatus according to claim 1, wherein the color assignment unit makes a plurality of items of the feature amount correspond to any one of three axes on a three-dimensional color space, and determines a position on the color space according to a specific value of each item of the feature amount to determine a color.

7. The image processing apparatus according to claim 6, wherein the color assignment unit performs gamma conversion in a case of determining a position on the color space according to the feature amount.

8. The image processing apparatus according to claim 1, further comprising:
a display control unit that performs control to display the composite image on a display screen.

9. The image processing apparatus according to claim 8, wherein, on the display screen, the original image and the composite image are able to be displayed in parallel or selectively.

10. The image processing apparatus according to claim 8, wherein the display control unit is able to output the display screen to a multi-monitor.

11. An image processing method, comprising:
an image signal acquisition step of acquiring an image signal obtained by imaging an observation target in a living body;
a structure region image generation step of generating a structure region image in which one or more structure regions are extracted from the acquired image signal;
a feature amount calculation step of calculating a shape feature amount of the structure region based on the structure region image;
a color assignment step of assigning a color corresponding to the feature amount to the structure region; and
an image combining step of generating a composite image by superimposing a reduced original image, which is obtained by performing processing for reducing at least one of a color or a contrast on an original image in which the observation target is drawn in color based on the image signal, and the structure region image subjected to the color assignment,
wherein a first structure region image showing a first structure region and a second structure region image showing a second structure region are generated in the structure region image generation step,
wherein a first reduced original image and a second reduced original image are generated in the reduced original image generation step, and
wherein, as the composite image, a first composite image obtained by combining the first structure region image and the first reduced original image and a second composite image obtained by combining the second structure region image and the second reduced original image are generated in the image combining step.

* * * * *